United States Patent [19]
Lee et al.

[11] Patent Number: 6,136,953
[45] Date of Patent: Oct. 24, 2000

[54] SMOOTH MUSCLE CELL LIM PROTEIN

[75] Inventors: Mu-En Lee, Newton, Mass.; Edgar Haber, Salisbury, N.H.; Mukesh Jain, West Newton; Shaw-Fang Yet, Andover, both of Mass.

[73] Assignee: President and Fellows of Harvard College, Cambridge, Mass.

[21] Appl. No.: 09/054,298

[22] Filed: Apr. 2, 1998

Related U.S. Application Data

[62] Division of application No. 08/616,368, Mar. 15, 1996, Pat. No. 5,767,262.

[51] Int. Cl.⁷ .................................................. C07K 14/435
[52] U.S. Cl. .............................. 530/350; 530/350; 435/6; 435/69.1; 435/92.2; 536/23.1; 536/23.5; 536/25.5; 514/44; 514/2; 935/23; 424/93.21
[58] Field of Search .................... 536/23.5, 23.1, 536/25.5; 435/69.1, 325, 92.2, 6; 514/44, 2; 935/23; 530/350; 424/93.21

[56] References Cited

PUBLICATIONS

Weiskirchen et al. Direct Submission to the EMBL Data Library, May 8, 1995.
Weiskirchen et al. Oncogene, vol. 8, pp. 2317–2324, Apr. 16, 1993.
Arber et al. "Muscle LIM Protein a Novel Essential Regulator of Myogenesis, Promotes Myogenic Differentiation", *Cell*, 79:221–31 (1994).
Crawford et al. "Biochemical and Molecular Characterization of the Chicken Cysteine–rich Protein, a Developmentally Regulated LIM–Domain Protein That Is Associated with the Actin Cytoskeleton", *J. Cell. Biol.*, 124:117–27 (1994).
Hillier et al. GenBank Accession #N39473, Jan. 19, 1996.
Libby et al. "Biology of Disease: Involvement of the Immune System in Human Atherogenesis: Current Knowledge and Unanswered Questions", *Lab. Investig.*, 64:5–15 (1991).
Munro et al., "Biology of Disease: The Pathogenesis of Atherosclerosis: Atherogenesis and Inflammation", *Lab. Invest.*, 58:249–61 (1988).
Ross, "The Pathogenesis of Atherosclerosis: a Perspective for the 1990s", *Nature*, 362:801–809 (1993).
Sadler et al., "Zyxin and cCRP: Two Interactive LIM Domain Proteins Associated with the Cytoskeleton", *J. Cell. Biol.*, 119:1573–87 (1992).
Tsai et al. "Promotion of Vascular Smooth Muscle Cell Growth by Homocysteine: A Link to Atherosclerosis", *PNAS USA*, 91:6369–73 (1994).
Tsai et al., "Induction of Cyclin A Gene Expression by Homocysteine in Vascular Smooth Muscle Cells", *J. Clin. Invest.*, 97:146–53 (1996).
Wang et al., "Analysis of the Human Cysteine–Rich Protein Gene (CSRP) Assignment to Chromosome 1q24–1q32, and Identification of an Associated MspI Polymorphism", *Genomics*, 14:391–97 (1992).
Wang et al. "Human Cysteine–rich Protein: A Member of the Lim/Double–Finger Family Displaying Coordinate Serum Induction with c–myc", *J. Biol. Chem.*, 267:9176–84 (1992).
Warren et al., "The Oncogenic Cysteine–Rich LIM Domain Protein Rbtn2 is Essential for Erythroid Development" *Cell*, 78:45–57 (1994).
Weiskirchen et al., "The Cysteine–rich Protein Family of Highly Related LIM Domain Proteins", *J. Biol. Chem.* 270:28946–54 (1995).
Weiskirchen et al. "Suppression in transformed avian fibroblasts of a gene (crp) encoding a cysteine–rich protein containing LIM domains", *Oncogene*, 8:2317–2324 (1993).

*Primary Examiner*—Christopher S. F. Low
*Assistant Examiner*—Hope A. Robinson
*Attorney, Agent, or Firm*—Mintz, Levin, Cohn, Ferris Glovsky and Popeo, P.C.; Ivor R. Elrifi; Ingrid A. Beattie

[57] ABSTRACT

A substantially pure DNA comprising a sequence encoding a smooth muscle cell LIM (SmLIM) polypeptide, methods of diagnosing vascular injury by detecting a decrease in SmLIM gene expression, and methods of inhibiting vascular smooth muscle cell proliferation.

3 Claims, 6 Drawing Sheets

HOECHST 33258

9E10

SMOOTH MUSCLE CELL LIM PROTEIN

This application is a Division of Ser. No. 08/616,368, filed Mar. 15, 1996 now U.S. Pat. No. 5,767,262.

STATEMENT AS TO FEDERALLY SPONSORED RESEARCH

This invention was made with U.S. Government support under National Institutes of Health grants RO1 GM53249, KO8 HL03274, and KO8 HL03194. The government has certain rights in the invention.

BACKGROUND OF THE INVENTION

The invention relates to diagnosis and treatment of vascular injury.

In their normal state, vascular smooth muscle cells regulate vessel tone and blood pressure. Unlike skeletal muscle and cardiac muscle cells, these cells are not terminally differentiated. In response to mechanical, chemical, or immunologic injury (Libby et al., 1991, Lab Invest. 64:5–15; Munro et al., 1988, Lab Invest. 58:249–261; Ross, R., 1993, Nature 362:801–809; Tsai et al., 1994, Proc. Natl. Acad. Sci. U.S.A 91:6369–6373; and Tsai et al., 1996, Clin. Invest. 97:146–153), the phenotype of these cells changes rapidly from that of a differentiated, quiescent cell to that of a dedifferentiated, proliferating cell. Although vascular smooth muscle cell proliferation is a hallmark of arteriosclerosis, the leading cause of death in developed countries, little is known about the molecular mechanisms regulating this phenotypic change.

SUMMARY OF THE INVENTION

The invention is based on the identification and characterization of a smooth muscle cell LIM (SmLIM) polypeptide which is expressed preferentially in arterial smooth muscle cells. SmLIM expression was found to decrease as vascular smooth muscle cells changed from a quiescent, differentiated phenotype to a proliferative phenotype in response to vascular injury The invention features a substantially pure DNA containing a sequence which encodes a SmLIM polypeptide. By he term "SmLIM" is meant a polypeptide that contains at least two LIM domains, lacks a homeobox domain and a protein kinase domain, and inhibits proliferation of vascular smooth muscle cells. By "substantially pure DNA" is meant DNA that is free of the genes which, in the naturally-occurring genome of the organism from which the DNA of the invention is derived, flank the SmLIM gene. The term therefore includes, for example, a recombinant DNA which is incorporated into a vector, into an autonomously replicating plasmid or virus, or into the genomic DNA of a procaryote or eucaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. A "LIM domain" is defined by the amino acid consensus sequence $CX_2CX_{17\pm1}HX_2CX_2CX_2CX_{17\pm1}CX_2C/D/H$ (SEQ ID NO:18).

The SmLIM of the invention preferably has at least 85% sequence identity with SEQ ID NO:1, and more preferably at least 90% (e.g., at least 95%). The DNA may encode a naturally occurring mammalian SmLIM polypeptide such as a human, rat, mouse, guinea pig, hamster, dog, cat, pig, cow, goat, sheep, horse, monkey, or ape SmLIM. For example, the SmLIM may be a human, e,g, a polypeptide which includes the amino acid sequence of SEQ ID NO:1. More preferably, the DNA includes the nucleotide sequence of SEQ ID NO:2. The DNA may contain a strand which hybridizes at high stringency to a DNA probe having a portion or all of the nucleotide sequence of SEQ ID NO:2, or the complement thereof. The probe to which the DNA of the invention hybridizes preferably consists of at least 20 nucleotides, more preferably 40 nucleotides, even more preferably 50 nucleotides, and most preferably 100 nucleotides or more (up to 100%) of the nucleotide sequence of SEQ ID NO:2, or the complement thereof. Such a probe is useful for detecting expression of a SmLIM transcript in a cell by a method including the steps of (a) contacting mRNA obtained from the cell with the labeled hybridization probe; and (b) detecting hybridization of the probe with the mRNA transcript. The invention also includes a substantially pure strand of DNA containing at least 15 nucleotides (preferably 20, more preferably 30, even more preferably 50, and most preferably all) of SEQ ID NO:2.

Hybridization is carried out using standard techniques such as those described in Ausubel et al., Current Protocols in Molecular Biology, John Wiley & Sons, (1989). "High stringency" refers to DNA hybridization and wash conditions characterized by high temperature and low salt concentration, e.g., wash conditions of 65° C. at a salt concentration of approximately 0.1×SSC. "Low" to "moderate" stringency refers to DNA hybridization and wash conditions characterized by low temperature and high salt concentration, e.g. wash conditions of less than 60° C. at a salt concentration of at least 1.0×SSC. For example, high stringency conditions may include hybridization at about 42° C., and about 50% formamide; a first wash at about 65° C., about 2×SSC, and 1% SDS; followed by a second wash at about 65° C. and about 0.1% ×SSC. Lower stringency conditions suitable for detecting DNA sequences having about 50% sequence identity to a SmLIM gene are detected by, for example, hybridization at about 42° C. in the absence of formamide; a first wash at about 42° C., about 6×SSC, and about 1% SDS; and a second wash at about 50° C., about 6×SSC, and about 1% SDS.

The invention also includes a substantially pure DNA encoding a SmLIM, which DNA includes a nucleotide sequence having at least 50% sequence identity to SEQ ID NO:2. Preferably the DNA has at least 70%, more preferably at least 80%, more preferably at least 90%, more preferably at least 95%, and most preferably at least 99% identity to SEQ ID NO:2. The percent sequence identity of one DNA to another is determined by standard means, e.g., by the Sequence Analysis Software Package developed by the Genetics Computer Group (University of Wisconsin Biotechnology Center, Madison, Wis.) (or an equivalent program), employing the default parameters thereof.

The DNA may be operably linked to regulatory sequences, e.g., a promoter, for expression of the polypeptide. Preferably, the promoter is vascular cell-specific, more preferably, it is vascular smooth muscle cell-specific, and most preferably, it is arterial smooth muscle cell-specific. By "operably linked" is meant that a coding sequence and a regulatory sequence(s) are connected in such a way as to permit gene expression when the appropriate molecules (e.g., transcriptional activator proteins) are bound to the regulatory sequence(s). By "promoter" is meant a minimal DNA sequence sufficient to direct transcription. Promoters may be constitutive or inducible.

The invention includes a substantially pure DNA containing a sequence at least 50% identical to SEQ ID NO:3, which regulates arterial smooth muscle cell-specific transcription of a polypeptide-encoding sequence to which it is operably linked. Preferably, the DNA is at least 75% identical, more preferably at least 90% identical, more preferably at least 95%, and most preferably 100% identical to SEQ ID NO:3. The DNA may be operably linked to a heterologous polypeptide-encoding sequence and may be used in a method of directing arterial smooth muscle cell-specific expression of the polypeptide, e.g., by introducing the DNA linked to the coding sequence into an arterial cell. By the term "heterologous polypeptide" is meant a polypeptide other than a SmLIM polypeptide.

A cell which contains a recombinant SmLIM polypeptide-encoding DNA is also within the invention. The cell may be eucaryotic or procaryotic. A method of making a SmLIM polypeptide includes the steps of (a) providing the cell which contains SmLIM polypeptide-encoding DNA, and (b) culturing it under conditions permitting expression of the DNA. If the polypeptide is secreted by the cell, the SmLIM polypeptide produced can be recovered from the culture supernatant of the cell culture. If the polypeptide is not secreted, the polypeptide can be recovered by lysing the cultured cells.

The invention also includes a substantially pure human SmLIM polypeptide. Preferably, the amino acid sequence of the polypeptide is at least 90% identical, more preferably at least 95% identical, more preferably at least 99% identical to the amino acid sequence of SEQ ID NO:1. Most preferably, the amino acid sequence of the polypeptide includes SEQ ID NO:1. By a "substantially pure polypeptide" is meant a polypeptide which is separated from those components (proteins and other naturally-occurring organic molecules) which naturally accompany it. Typically, the polypeptide is substantially pure when it constitutes at least 60%, by weight, of the protein in the preparation. Preferably, the protein in the preparation consists of at least 75%, more preferably at least 90%, and most preferably at least 99%, by weight, a SmLIM polypeptide. A substantially pure SmLIM polypeptide may be obtained, for example, by extraction from a natural source (e.g., an arterial smooth muscle cell); by expression of a recombinant nucleic acid encoding a SmLIM polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components even without further purification steps. Accordingly, substantially pure polypeptides include recombinant polypeptides derived from a eucaryote but produced in E. coli or another procaryote, or in a eucaryote other than that from which the polypeptide was originally derived.

The invention also includes diagnostic methods. For example, one can detect injury in a sample of vascular tissue by determining the level of SmLIM gene expression in the tissue sample, and comparing it to the level of expression in a control sample of vascular tissue. This determination may be made using SmLIM-specific DNA probes to detect the level of gene transcription or using SmLIM-specific antibodies to detect the level of gene product in the cells. A decrease in the level of expression of SmLIM compared to the level in uninjured control vascular tissue indicates the presence of a vascular injury.

Methods of therapy are also within the invention. A method of inhibiting arterial smooth muscle cell proliferation in a mammal may include the steps of identifying a mammal in need of such inhibition, and introducing either SmLIM or a SmLIM-encoding DNA into an artery of the mammal. One can inhibit neointima formation after balloon angioplasty in a mammal by contacting an artery of the mammal with a SmLIM or SmLIM-encoding DNA prior to, during, or immediately after angioplasty to reduce proliferation of arterial smooth muscle cells in the mammal, particularly at the site of vascular injury treated by the angioplasty procedure. Preferably, the mammal is a human, and the SmLIM polypeptide is a human SmLIM polypeptide.

A method of screening candidate compounds to identify a compound capable of increasing expression of a SmLIM polypeptide in vascular smooth muscle cells is also within the invention. For example, an in vitro method may include the steps of (a) providing a vascular smooth muscle cell, e.g., a human arterial smooth muscle cell; (b) contacting the smooth muscle cell with a candidate compound; and (c) determining the amount of SmLIM expression by the vascular smooth muscle cell. The screening method can also be carried out in vivo, e.g., in an animal subjected to a vascular injury, and then treated with the candidate compound or a placebo. An increase in the amount of expression in the presence of the candidate compound compared to that in the absence of the candidate compound indicates that the candidate compound increases expression of a SmLIM polypeptide in vascular smooth muscle cells. An increase of SmLIM expression correlates with an inhibition in vascular smooth muscle cell proliferation. Expression may be determined by measuring gene transcription, e.g., in a Northern blot assay, or by measuring the amount of SmLIM polypeptide in the cell, e.g., by immunoblotting.

Other features and advantages of the invention will be apparent from the following detailed description, and from the claims.

DETAILED DESCRIPTION

Cell Culture and Reagents

Figure 1:
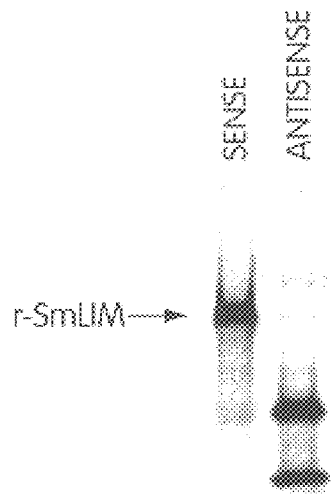
FIG. 1 is a photograph of an sodium dodecyl sulfate-polyacrylamide gel electrophoresis (SDS-PAGE) analysis of proteins. The entire rat (r-SmLIM) open reading frame was cloned in the sense and antisense orientations into the eucaryotic expression vector PCRIII. After in vitro transcription and translation with wheat germ lysate, the protein was resolved on a 10% SDS-PAGE Tricine gel. The single intense band in the sense lane (arrow) represents full-length SmLIM at 21 kDa.

Aortic smooth muscle cells were harvested from the thoracic aorta of adult male Sprague-Dawley rats (200–250 g) by enzymatic digestion. COS-7 (CRL 1651) and 10T1/2 (CCL 226) cells were obtained from the American Type Cell Culture Collection. Rat aortic smooth muscle cells were grown in DME medium (JRH Biosciences, Lenexa, Kans.) supplemented with 10% FCS, penicillin (100 U/ml), streptomycin (100 μg/ml), and 25 mM Hepes (pH 7.4) in a humidified incubator (37° C., 5% $CO_2$). COS-7 and 10T1/2 cells were grown similarly, with the exceptions that DME was supplemented with Serum Plus (Hyclone, Logan, Utah) for the former and BME (JRH Biosciences) was substituted for DME for the latter. Embryonic stem cells (D3) were cultured using known methods. Cells were cultured and maintained in an undifferentiated state with leukemia inhibitory factor using known methods, e.g., Doetschman et al., 1985, J. Embryol. Exp. Morph. 87:27–45. PDGF-BB was purchased from Collaborative Biomedical Products (Bedford, Mass.).

Cloning and Sequencing of r-SmLIM, Mouse SmLIM (m-SmLIM) and h-SmLIM

The full-length rat muscle LIM protein (MLP) cDNA was amplified from rat heart RNA by the reverse transcriptase PCR. Forward (5'GAGTCTTCACCATGCCGAAC3' SEQ ID NO:4) and reverse (5'CTCTCCCACCCCAAAAATAG3' SEQ ID NO:5) primers, designed according to the published rat MLP sequence (Arber et al., 1994, Cell 79:221–231), were used to amplify a 801-bp fragment. The PCR fragment was then subcloned and sequenced by the dideoxy chain termination method. The rat-MLP fragment was used to screen a rat neonatal aortic cDNA library in λgt11. Approximately 1.6 million phage clones were plated, transferred to nitrocellulose paper, and screened at low stringency. One out of nine isolated clones encoded the partial sequence of a novel LIM protein, r-SmLIM. This partial clone was then used to screen a rat smooth muscle cDNA library in λZAP (Clontech) to obtain the full-length clone. The same partial rat clone was also used to screen a human aortic λgt11 cDNA library to obtain the human sequence and a murine library to obtain the murine sequence. The sequences of several partially overlapping clones were compiled to obtain the full-length h-SmLIM sequence. Both strands of the entire r-SmLIM and h-SmLIM cDNAs were sequenced by the dideoxy chain termination method or on an automated DNA Sequencer (Licor, Lincoln, Nebr.) according to the manufacturer's instructions.

The nucleotide sequences have been submitted to the GENBANK™/EMBL Data Bank with accession numbers U44948 (r-SmLIM) and U46006 (h-SmLIM).

Cellular Localization of r-SmLIM

To construct the expression plasmid Myc-SmLIM/pCR3, DNA encoding a c-Myc peptide tag (EQKLISEED) (SEQ ID NO:6) was added in frame to the r-SmLIM open reading frame at the N-terminus using PCR techniques. This hybrid DNA fragment was then cloned into the eucaryotic expression vector pCR3 (Invitrogen). COS-7 and 10T1/2 cells were transiently transfected with the Myc-SmLIM/pCR3 plasmid using the DEAE-dextran method known in the art. The transfected cells were grown on chamber slides and fixed with 4% paraformaldehyde in PBS. Immunostaining was performed 48 h after transfection with an anti-c-Myc monoclonal antibody (e.g., 9E10; Oncogene) followed by a rhodamine-conjugated goat anti-mouse IgG secondary antibody. Nuclear counterstaining was performed with Hoechst 33258 according to the manufacturer's instructions.

Chromosomal Localization of h-SmLIM

The chromosomal location of h-SmLIM was determined using the BIOSMAP Somatic Cell Hybrid blot (BIOS Laboratories, Conn.), which contains DNA from 20 somatic cell hybrid cell lines plus 3 control DNAs (human, hamster, and mouse). A full-length h-SmLIM fragment was randomly primed and hybridized as recommended by the manufacturer. The blot was washed according to the manufacturer's instructions and then exposed to Kodak XAR film at −80° C.

RNA Extraction and RNA Blot Analysis

Total RNA was isolated from cultured cells, rat organs, embryonic stem cells, and mouse embryos by guanidinium isothiocyanate extraction and centrifugation through cesium chloride. The mouse embryo samples (7–10 days old) included placenta and yolk sac tissue. Carotid artery total RNA was obtained by the RNA-Zol method (Cinna/Biotecx Laboratories International, Houston, Tex.) from adult male Sprague-Dawley rats that had been subjected to balloon injury (Zivic-Miller Company, Zelienople, Pa.). Human poly A+ RNA was purchased from Clontech Laboratories (Palo Alto, Inc. Calif.). All RNA was fractionated on a 1.3% formaldehyde-agarose gel and transferred to nitrocellulose filters. The filters were then hybridized with the appropriate $^{32}$P-labeled, random primed cDNA probes using standard methods. The hybridized filters were washed in 30 mM sodium chloride, 3 mM sodium citrate, and 0.1% SDS at 55° C. and autoradiographed on Kodak XAR film at −80° C. To control for differences in RNA loading, the blots were hybridized with an 18S-specific or 28S-specific oligonucleotide probe. The filters were scanned and radioactivity was measured on a PhosphorImager running the ImageQuant software (Molecular Dynamics, Sunnyvale, Calif.).

In Vitro Transcription and Translation

The complete r-SmLIM open reading frame was cloned into the eucaryotic expression vector pCR3 (Invitrogen). In vitro transcription and translation was performed in the TNT-coupled wheat germ extract system (Promega, Madison, Wis.) according to the manufacturer's instructions. The transcribed and translated products were resolved on a 10% SDS-PAGE Tricine gel, and autoradiography was performed with Kodak BMR film at room temperature.

In Situ Hybridization

Rat SmLIM mRNA was hybridized in situ using standard methods. Adult male Sprague-Dawley rats were perfused with 4% paraformaldehyde. Organs were then postfixed with 4% paraformaldehyde, soaked in 30% sucrose until the tissue sank, embedded in optimum cutting temperature (O.C.T.) compound, and stored in isopentane at −80° C. Tissue sections were cut at a thickness of 5 microns. SmLIM mRNA was detected by hybridization with a [$^{35}$S]UTP-labeled antisense cRNA probe synthesized with the SP6 RNA polymerase from HindIII-linearized r-SmLIM in Bluescript II SK+. For control experiments, a [$^{35}$S]UTP-labeled sense cRNA probe was synthesized under the same conditions. RNA probes were degraded to a length of approximately 100–200 nucleotides by partial hydrolysis for 15 min at 600° C. in 80 mM NaHCO$_3$ and 120 mM Na$_2$CO$_3$. After hybridization, the tissue sections were washed under moderately stringent conditions (Lee et al., 1993, Endocrinology 132:2136–2140). The dried tissue sections were then dipped into Kodak NTB2 emulsion (Eastman Kodak, Rochester, N.Y.) and exposed for 2–4 days at 40° C. Counterstaining was performed with hematoxylin-eosin.

Isolation and Characterization of r-SmLIM and h-SmLIM cDNA

The nucleotide sequence of the r-SmLIM cDNA revealed a 582-bp open reading frame encoding a 194 amino-acid protein. Analysis of this frame identified two LIM domains separated by a glycine-rich region and a putative nuclear localization signal.

TABLE 1 shows the complete nucleotide (upper line) and deduced amino acid (lower line) sequences of r-SmLIM. Residues composing the two LIM domains are in boldface, a putative nuclear localization signal is underlined, and the polyadenylation signal is underlined and in italics. The nucleotide sequence flanking the putative initiation methionine complied with the Kozak consensus sequence for initiation of translation. A 21 kDa polypeptide was encoded by the r-SmLIM open reading frame.

The entire r-SmLIM cDNA was cloned into the PCRIII eucaryotic expression vector. In vitro transcription and translation (Promega) of this expression plasmid with wheat germ lysate revealed a protein product of 21-kDa (FIG. 1).

Conservation of SmLIM Among Species

To determine whether SmLIM was conserved across species, the human, rat, and mouse homologues were compared. A comparison of the h-SmLIM and r-SmLIM open reading frames revealed 93% identity at the cDNA level and 99% identity at the amino acid level (TABLES 2 AND 3). Comparison of the open reading frames of murine SmLIM (m-SmLIM) and r-SmLIM revealed 97% identity at the cDNA level and 100% identity at the amino acid level (TABLE 3). A GENBANK™ search indicated that SmLIM shares homology with the cysteine-rich protein (CRP) family. TABLE 2 compares r-SmLIM and h-SmLIM with their rat and human CRP counterparts and rat MLP. Although an amino acid sequence comparison of r-SmLIM and h-SmLIM shows 99% identity (TABLE 3), a comparison of r-SmLIM with r-CRP shows only 79% identity. These data indicate that SmLIM and CRP are related but different genes.

TABLE 2 shows a sequence alignment of rat (r)-SmLIM and human (h)-SmLIM proteins to the LIM proteins r-CRP, h-CRP, and r-MLP. Consensus sequence indicates residues conserved in all five proteins. Cysteine and histidine residues composing LIM domains are underlined.

TABLE 1

| | |
|---|---|
| 1 | ACGAGCTAGACCTCCCTAGCTCCGCCCGCCGCGTGCTCCCGCCTCCCACTCGGAATGCCT |
| | M P |
| 61 | GTCTGGGGCGGTGGAAATAAGTGCGGGGCCTGCGGGAGAACCGTGTACCACGCTGAAGAG |
| | V W G G G N K C G A C G R T V Y H A E E |
| 121 | GTGCAGTGTGATGGGCGGACGTTCCACCGCTGCTGCTTTCTGTGCATGGTTTGCAGGAAA |
| | V Q C D G R T F H R C C F L C M V C R K |
| 181 | AATTTAGACAGCACAACAGTGGCAATTCATGATGAAGAGATCTACTGCAAATCATGCTAC |
| | N L D S T T V A I H D E E I Y C K S C Y |
| 241 | GGAAAGAAGTATGGACCAAAAGGCTATGGTTATGGCCAGGGCGCTGGCACGCTCAACATG |
| | G <u>K K Y G P K</u> G Y G Y G Q G A G T L N M |
| 301 | GACCGTGGTGAGAGGCTGGGCATCAAGCCAGAGAGTGCTCAACCTCACAGGCCTACAACA |
| | D R G E T L G I K P E S A Q P H R P T T |
| 361 | AATCCAAACACTTCTAAATTTGCCCAGAAATATGGAGGTGCTGAGAAGTGCTCCAGATGT |
| | N P N T S K F A Q K Y G G A E K C S R C |

TABLE 1-continued

```
421 GGGGATTCTGTGTATGCTGCTGAGAAGATCATTGGAGCTGGAAAGCCCTGGCACAAAAC
     G   D   S   V   Y   A   A   E   K   I   I   G   A   G   K   P   W   H   K   N
481 TGTTTCCGATGTGCCAAGTGTGGGAAGAGTCTGGAGTCTACAACTCTGACTGAGAAGGAA
     C   F   R   C   A   K   C   G   K   S   L   E   S   T   T   L   T   E   K   E
541 GGTGAAATCTACTGTAAAGGGTGCTACGCAAAGAACTTTGGGCCCAAGGGATTCGGCTAT
     G   E   I   Y   C   K   G   C   Y   A   K   N   F   G   P   K   G   F   G   Y
601 GGTCAAGGAGCAGGGGCCCTTGTTCATGCTCAGTAGTGGTGTAAACCCAGTAAGCATGGC
     G   Q   G   A   G   A   L   V   H   A   Q   *                    (SEQ ID NO: 8)
661 AAAGAACCTCCATTAATGTGGATGGCCTTACCGCACTCAGGCTGTGCATCGGCCAGCACT
721 CAGCACTGTGTAGCACACACGCTATGTGCACAATCGGGCTGGACAGGAAGCACTACACTC
781 TCCTGCCCATCCGCTAACGTTTAAGAACGTTCTTTTACATTTGG*AATAAA*ATTTTGGTTT
841 GATTTGAAAAAAAAAAAAAAAAAAAAAAAAAAAAAAAAAAAAAA (SEQ ID NO: 7)
```

TABLE 2

```
              1         .         .         .         .        50
  r-SmLIM    MPVWGGGNKCGACGRTVYHAEEVQCDGRTFHRCCFLCMVCRKNLDSTTVA
  h-SmLIM    MPVWGGGNKCGACGRTVYHAEEVQCDGRSFHRCCFLCMVCRKNLDSTTVA
    r-CRP    MPNWGGGKKCGVCQKTVYFAEEVQCEGNSFHKSCFLCMVCKKNLDSTTVA
    h-CRP    MPNWGGGKKCGVCQKTVYFAEEVQCEGNSFHKSCFLCMVCKKNLDSTTVA
    r-MLP    MPNWGGGAKCGACDKTBYHAEEIQCNGRSFHKTCFHCMACRKALDSTTVA
Consensus    MPNWGGGNKCGNCNNTVYNAEEVQCNGNNFHNNCFNCMNCNJNKDSTTVA 51        .         .         .         .       100
  R-SmLIM    IHDEEIYCKSCYGKKYGPKGYGYGQGAGTLNMDRGERLGIKPESAQPH R
  h-SmLIM    IHDEEIYCKSCYGKKYGPKGYGYGQGAGTLNMDRGERLGIKPESVQPH R
    r-CRP    VHGEEIYCKSCYGKKYGPKGYGYGQGAGTLSMDKGESLGIKHEEAPGH R
    h-CRP    VHGEEIYCKSCYGKKYGPKGYGYGQGAGTLSTDKGESLGIKHEEAPGH R
    r-MLP    AHESEIYCKBCYGRKYGPKGIGFGQGAGCLSTDTGEHLGLQFQQSPKPAR
Consensus    NHNNEIYCKNCYGNKYGPKGNGYGQGAGNINNDNGENLGNNNNNNNNNR 101       .         .         .         .       150
  r-SmLIM    PTTNPNTSKFAQKYGGAEKCSRCGDSVYAAEKIIGAGKPWHKNCFRCAKC
  h-SmLIM    PTTNPNTSKFAQKYGGAEKCSRCGDSVYAAEKIIGAGKPWHKNCFRCAKC
    r-CRP    PTTNPNASKFAQKIGGSERCPRCSQAVYAAEKVIGAGKSWHKSCFRCAKC
    h-CRP    PTTNPNASKFAQKIGGSERCPRCSQAVYAAEKVIGAGKSWHKACFRCAKC
    r-MLP    AATTSNPSKFSAKFGESEKCPRCGKSVYAAEKVMGGGKPWHKTCFPCAIC
Consensus    NNTNNNNSKFNNKNGNNENCNRCNNNVYAAEKNNGNGKNWHKNCFNCANC 151       .         .         .194
  r-SmLIM    GKSLESTTLTEKEGEIYCKGCYAKNFGPKGFGYGQGAGALVHAQ       (SEQ ID NO: 8)
  h-SmLIM    GKSLESTTLTEKEGEIYCKGCYAKNFGPKGFGYGQGAGALBHAQ       (SEQ ID NO: 1)
    r-CRP    GKGLESTTLADKDGEIYCKGCYAKNFGPKGFGFGQGAGALBHSE       (SEQ ID NO: 9)
    h-CRP    GKGLESTTLADKDGEIYCKGCYAKNFGPKGFGFGQGAGALBHSE       (SEQ ID NO: 10)
    r-MLP    GKSLESTNVTDKDGELYCKBCYAKNFGPTGIGFGGLTHQVEKKE       (SEQ ID NO: 11)
Consensus    GKNLESTNNNNKNGENYCKNCYAKNFGPNGNGNGNNNNNNNNNN       (SEQ ID NO: 12)
```

TABLE 3

|  |  | Nucleotides (%) | Amino Acids (%) |
|---|---|---|---|
| r-SmLIM versus | m-SmLIM | 97 | 100 |
|  | h-SmLIM | 93 | 99 |
|  | r-CRP | 73 | 79 |
|  | h-CRP | 72 | 79 |
|  | r-MLP | 65 | 65 |

TABLE 3 shows the percentage nucleotide and amino acid identity of r-SmLIM versus mouse m-SmLIM and h-SmLIM homologues, r-CRP, h-CRP, and r-MLP.

TABLE 4 shows the nucleotide sequence of the h-SmLIM cDNA.

TABLE 4

```
  1 ATGCCTGTCT GGGGAGGTGG AAACAAGTGT GGGGCCTGTG GGAGGACCGT (SEQ ID NO: 2)
 51 GTACCACGCA GAAGAGGTGC AGTGTGATGG CAGGAGCTTC CACCGCTGCT
101 GCTTTCTCTG CATGGTTTGC AGGAAAAATT TAGATAGCAC AACAGTGGCA
151 ATTCACGATG AAGAGATCTA CTGCAAATCC TGCTACGGAA AGAAGTATGG
201 GCCAAAAGGC TACGGTTATG GCCAGGGCGC TGGCACGCTt aacatggacc
```

TABLE 4-continued

```
251 gtggcgagag gctgggcatc aaaccagaga gtgttcagcc tcacaggcct
301 acaacaaatc caaacacttc taaatttgct cagaaatatg gaggtgctga
351 gaAGTGTTCC AGATGTGGGG ATTCTGTATA TGCTGCCGAG AAGATAATTG
401 GAGCTGGAAA GCCCTGGCAC AAAAACTGTT TCCGATGTGC AAAGTGTGGG
451 AAGAGTCTTG AATCAACAAC TCTGACTGAA AAAGAAGGTG AAATCTATTG
501 TAAAGGATGC TATGCAAAGA ACTTTGGGCC CAAGGGATTT GGCTATGGCC
551 AAGGAGCAGG GGCTCTTGTT CATGCCCAGT AAGATGTAAA CCCTGAACTA
601 AACATCACAC ACTGAGAATC TCTTCATAAT CTAGGCACAG ATAATCTTTA
651 ACCCGGAATT CCGCCGATAC TGACGGGCTC CAGGAGTCGT CGCCACCAAG
701 CCGAATTCCA GCACACTGGC GGcCGTTACT AGTGGATCCG A
```

TABLE 5 shows the nucleotide sequence of m-SmLIM cDNA and amino acid sequence of the m-SmLIM polypeptide.

TABLE 5

```
     AGTCTCCGGATCcGCCCGCGGCTTTCCTCGGTCAGACCTCGTTAGCTCCGCCCGCCGCGT  60

GCTCCCTCCTCCCACTCGGAATGCCTGTCTGGGGCGGTGGAAATAAGTGCGGGGCCTGCG 120
  1                       M   P   V   W   G   G   N   K   C   G   A   C   G

GGAGAACCGTGTACCACGCGGAAGAGGTGCAGTGCGATGGGCGGACGTTCCATCGCTGCT 180
 15   R   T   V   Y   H   A   E   E   V   Q   C   D   G   R   T   F   H   R   C   C

GCTTCCTGTGCATGGTTTGCAGGAAAAATTTAGACAGCACAACAGTGGCGATTCATGATG 240
 35   F   L   C   M   V   C   R   K   N   L   D   S   T   T   V   A   I   H   D   E

AAGAGATCTACTGCAAATCCTGCTACGGAAAGAAGTATGGACCAAAAGGCTATGGTTATG 300
 55   E   I   Y   C   K   S   C   Y   G   K   K   Y   G   P   K   G   Y   G   Y   G

GCCAGGGCGCTGGCACGCTCAACATGGACCGCGGTGAGAGACTGGGCATCAAGCCAGAGA 360
 75   Q   G   A   G   T   L   N   M   D   R   G   E   R   L   G   I   K   P   E   S

GTGCTCAACCTCACAGGCCTACGACAAATCCAAACACTTCTAAATTTGCCCAGAAATATG 420
 95   A   Q   P   H   R   P   T   T   N   P   N   T   S   K   F   A   Q   K   Y   G

GAGGAGCTGAGAAGTGTTCCAGGTGTGGGGATTCCGTGTATGCTGCGGAGAAGATCATTG 480
115   G   A   E   K   C   S   R   C   G   D   S   V   Y   A   A   E   K   I   I   G

GAGCTGGGAAGCCCTGGCACAAAAACTGTTTCCGGTGTGCCAAGTGTGGGAAGAGTCTGG 540
135   A   G   K   P   W   H   K   N   C   F   R   C   A   K   C   G   K   S   L   E

AGTCTACAACTCTGACTGAGAAAGAAGGCGAAATCTACTGTAAAGGGTGCTACGCAAAGA 600
155   S   T   T   L   T   E   K   E   G   E   I   Y   C   K   G   C   Y   A   K   N

ACTTTGGGCCCAAGGGATTTGGCTATGGTCAAGGGGCAGGGGCCCTTGTTCATGCTCAGT 660
175   F   G   P   K   G   F   G   Y   G   Q   G   A   G   A   L   V   H   A   Q   *
                                                              (SEQ ID NO: 13)

AATGGTGTGAACCAGTAAGCACGACAGAGAATCTCCATTACCAAACTGCAGATGGCGTTT 720

ATGGCGCTCACTACTGTGAAACAGCCAGCACTTGGCACTGGGCATCACCGAGCTGCCTGT 780

GGGGGCTGGACCGACAGCGCTGCACTCTCCCGCCCACTCACTAGCGTCTAAGAGCATTCT 840
                                                              (SEQ ID NO: 14)
```

The number of nucleotide and amino acid sequence positions are indicated in the right and left margins, respectively. The potential nuclear localization signal is underlined. The conserved cysteine and histidine residues of the two LIM domains are in bold, and the adjacent glycine residues in the glycine-rich repeat are in italics.

TABLE 6 and 7 show the m-SmLIM promoter. In TABLE 6, the transcription start site is indicated with an arrow.

TABLE 6

```
  1  TGAGGAATGC AGCTCTTtCG CGACAGGAAA GCTGCGGATT CCAGAAGCCG  (SEQ ID NO:16)
 51  GGATTCTGAC CAGAGACTAT CTGCACCGGG GAGTCCTGCA CCCCGAGCTA
101  ACATATGgCG TTTGTGCAGT AAAAGGGTGG CGGGAATCCC ACGGGGCGAC
151  ACCGGATCTC GCTGGCTCCG GGCCGATCCT GAGTGCTCCG GACGTCCCGG
201  GACCGCGGGT AGGAGCAGCC GAGACGTGGG AGACTCGGAC GCGGGAAGCC
251  GCAGGAAGAG GCGGATTCCG GTCTTTTTGT CTCGGGGCCA GAGCaCGAAA
301  CCCGCAtCGG ATCCCCGAGC TCACGCCGGG CGGAGACCAT CGCACACCCG
351  AGGGGCATGA CCGATGGCTG AGTCGGAACA AGCCACGCCC AACATAAGTC
                                    →
401  TTTAAAAGCG GCACACGCG TCCCGCCAGT CTCCGGATCC GCCCGCCGGC
451  TTTCCTCGGT CAGACCTCGT TAGCTCCGCC CGCCGCGTGC TCCCTCCTCC
501  CACTCGGgtg agtcctaggc tc
```

TABLE 7

```
  1  TGAGGAATGC AGCTCTTtCG CGACAGGAAA GCTGCGGATT CCAGAAGCCG  (SEQ ID NO:3)
 51  GGATTCTGAC CAGAGACTAT CTGCACCGGG GAGTCCTGCA CCCCGAGCTA
101  ACATATGgCG TTTGTGCAGT AAAAGGGTGG CGGGAATCCC ACGGGGCGAC
151  ACCGGATCTC GCTGGCTCCG GGCCGATCCT GAGTGCTCCG GACGTCCCGG
201  GACCGCGGGT AGGAGCAGCC GAGACGTGGG AGACTCGGAC GCGGGAAGCC
251  GCAGGAAGAG GCGGATTCCG GTCTTTTTGT CTCGGGGCCA GAGCaCGAAA
301  CCCGCAtCGG ATCCCCGAGC TCACGCCGGG CGGAGACCAT CGCACACCCG
351  AGGGGCATGA CCGATGGCTG AGTCGGAACA AGCCACGCCC AACATAAGTC
401  TTTAAAAGCG GCACACGCG TCCCGCC
```

TABLE 8 shows the m-SmLIM genomic sequence.

TABLE 8

SmLIM-Genomic Sequence

EXON 1 AGTCTCCGGATCCGCCCGCGGCTTTCCTCGGTCAGACCTCGTTAGCTCCGCC
       CGCCGCGTGCTCCCTCCTCCCACTCGG(SEQ ID NO:19)

gtgagtcctaggctc...........gagctctgtgagtaagagcgatgtttcctccacgatatgc
       tagataaaaatctgggggtgggggtaaccagaagagggacaaagcaccttgtactaattgtttaa
       atatttaataaaggtctcatcaggaaacctaatagaggtctgcaccatttaatggttgtatgggaa
       tcacgcctttaaggcaaagatgagctttctctgctacagacta..........aagcatctgctag
       tacgcactgtctcgtggctgaagcagccggagggaactcgtaaaacaacgcatcctaatgcatcct
       ttgttccgcag(SEQ ID NOS:20,21,22)

EXON 2 CATGCCTGTCTGGGGCGGTGGAAATAAGTGCGGGGCCTGCGGGAGAACCGTGTACCACGCGGAAGA
        M  P  V  W  G  G  G  N  K  C  G  A  C  G  R  T  V  Y  H  A  E  E
       GGTGCAGTGCGATGGGCGGACGTTCCATCGCTGCTGCTGTTCCTGTGCA(SEQ ID NO:23)
        V  Q  C  D  R  T  F  J  R  C  C  F  L  C  M(SEQ ID NO:24)

gtgagtatggtcccctcccccttcagttcacctctggaagaaaaataacaatgctagctaagagaa
       atggtttagagtgacggggttttttgtttgtttgttttttgtttaaccgctgagtcatctctcta
       gcccaatgcggtgttttatgtcattgatcttaagacgctgaggactgagccagagggaagaccacc
       tagccctcagttctggccagttggcttagcctttgtcacctctgtctgtgtcctcggg........
       ......gtcatttggaggcacctctgttttaagttaaagctatatatatatatatatatatata
       tatatatatatatatatatattcatattttaatgatgtttaaaatctatctaccctggggct
       tag(SEQ ID NOS:25,26)

EXON 3 TGGTTTGCAGGAAAAATTTAGACAGCACAACAGTGGCGATTCATGATGAAGAGATCTACTGCAAAT
         V  C  R  K  N  L  D  S  T  T  V  A  I  H  D  E  E  I  Y  C  K  S
       CCTGCTACGGAAAGAAGTATGGACCAAAAGGCTATGGTTATGGCCAGGGCGCTGGCACGCTCAACA
         C  Y  G  K  K  Y  G  P  K  G  Y  G  Y  G  Q  G  A  G  T  L  N  M
       TGGACCGCGGTGAGAGACTGGGCATCAAGCCAGAGAG(SEQ ID NO:27)
         D  R  G  E  R  L  G  I  K  P  E  S(SEQ ID NO:28)

gtgagagaatgttaccctcttaaaagcgggtagaacagctcctgtcgctcaggcaccaggagcctg
       catatttagtttaaactaagcaagcaaaataaaatgtgacctctactaaatactcatatgattact
       acgacgttctgtaacgtcataatattgacagttttgtatctaaaaatcttagtaatgaatgcaggg
       acttctagccctggttatatagcattttaactgatatcaggaaaacataaatctcaaggaactgac
       ttacttaatatcccatacgcactggagatcaaatatcttgaaatgagtgtctgaattctgagatcg
       ttctcatatgattaactgtccacggaaagtcctagtcactctttcctcaggaaattacatccttc
       aacttagaaattaaaaccatttcctcgttctgatgatttgagggacaaatcg............aa
       atgtttcacaatatacattacctctaaatcttcccatcaatgaaaactaaattcacaagaccccca
       aggctgtgtttgtagccagaactgggaaatcacggatgctcttttctgccctgtccccacctttccc
       agcaataagcaagctctgtgtgcacgccctatgtgcagtggtaaccctgtctgtgccctccagccg TABLE 8-continued

```
        ggccctggtctggtcttcctctgcgatcaggtctaaggaattcctcctcccagaggtcttctttag
        gactcaaaaccatggcctgccttttaacacacagattaaa..........cgaagctcctgttagc
        tcaggaggaacatttggagaaacactgcctcattttttctccgttcctccag(SEQ ID NOS:29,30,31)

EXON 4  TGCTCAACCTCACAGGCCTACGACAAATCCAAACACTTCTAAATTTGCCCAGAAATATGGAGGAGC
         A   Q   P   H   R   P   T   T   N   P   N   T   S   K   F   A   Q   K   Y   G   G   A
        TGAGAAGTGTTCCAGGTGTGGGGATTCCGTGTATGCTGCGGAGAAGATCATTGGAGCTGGGAAG(SEQ ID NO:32)
         E   K   C   S   R   C   G   D   S   V   Y   A   A   E   K   I   I   G   A   G   K(SEQ ID NO:33)

gtagggcgctgtctctaagtggtaactgcagcacacactcacacacaccacagggtgctgtctgtct
        ctaactggtaactgtaataaacacacacatacatacacaagcatacatagacacacacacacacac
        acacacatac...........ctgctcccagcaaacagcccttactggtggctagaagatatgac
        agcaaagaggccagctttctagctgagccaaaccgtagcctgaggaggctgcttgtgcgctggttt
        tcccagccacttgctgcatctagatcgagccaaaggaaacaagcctctcaatgtcctaactcagct
        gtctcttccag(SEQ ID NOS:34,35)

EXON 5  CCCTGGCACAAAAACTGTTTCCGGTGTGCCAAGTGTGGGAAGAGTCTGGAGTCTACAACTCTGACT
         P   W   H   K   N   C   F   R   C   A   K   C   G   K   S   L   E   S   T   T   L   T
        GAGAAAGAAGGCGAAATCTACTGTAAAG(SEQ ID NO:36)
         E   K   E   G   E   I   Y   C   K   G(SEQ ID NO:37)

gtaaaaactcggttctgctgtctgttagtgtcaccagaaagggagacatcgtgcactgttaccttt
        tgaaaatgagaccgacatcttaggacagtgattacttcttccattcctactgtgtgtgttaagtcc
        acacggctgggggatctggccgaatggtaaaagcttgcctatgtagcacattcacaaggaggccacg
        ctcagcacggcctccccaacctctgacttcctgctttaagccaagcatatgactacgtgagggtga
        cacacagaaggcagctggatttcagcctgcagctcatcacaatcctaacttggatgccgtgggaat
        tcctggactcgcttcaaacaaggatgctcatagcagagcccattttatatcttaaactgacctctg
        cagagcctccagttggcttttaaattaatggccatttgttagtgacctctgattaactctcccttt
        cctttgtag(SEQ ID NO:38)

EXON 6  GGTGCTACGCAAAGAACTTTGGGCCCAAGGGATTTGGCTATGGTCAAGGGGCAGGGGCCCTTGTTC
         C   Y   A   K   N   F   G   P   K   G   F   F   Y   G   Q   G   A   G   A   L   V   H
        ATGCTCAGTAATGGTGTGAACCAGTAAGCACGACAGAGAATCTCCATTACCAAACTGCAGATGGCG
         A   Q   *(SEQ ID NO:40)
        TTTATGGCGCTCACTACTGTGAAACAGCCAGCACTTGGCACTGGGCATCACCGAGCTGCCTGTGGG
        GGCTGGACCGACAGCGCTGCACTCTCCCGCCCACTCACTAGCGTCAAGAGCATTCTTTTACATTT
        GAAATAAAATTTTGGCTTG(SEQ ID NO:39)

atttgggtaccacctcttaattaacctttcagaggagctgttgtgattttagatgatgagaagtt
        atctggttccttcctccagtgaaaaccagtctcctgattaaaaaaaaaaaaaagaccgttttcttta
        aaaagacaatcaattcctttatgcagtaggctaacatttgcactctgagagctgaaaacgacattt
        tacttttgagattttcattcatatatatatatatatacatatatatatatatatatatatatat
        atatatatatatatacaaaacactccgtgga(SEQ ID NO:17)
```

SmLIM is a highly conserved, two-LIM-domain nuclear protein of the LIM-only class. Other members of this class include RBTN2, MLP, and CRP. Like SmLIM, RBTN2 and MLP are nuclear proteins with two LIM-domains, and they are highly conserved across species (Arber et al. 1994, Cell 79:221–231; Warren et al., 1994, Cell 78:45–57). CRP proteins also have two LIM-domains and show high cross-species conservation (Wang et al. 1992, J. Biol. Chem. 267:9176–9184; Weiskirchen et al., 1995, J. Biol. Chem. 270:28946–28954). Sequence comparisons of SmLIM and CRP suggest that the two gene families are related yet distinct (TABLES 2 and 3). In contrast with SmLIM, which is a nuclear protein (FIGS. 2A and 2B), CRP has been localized to the cytoskeletal adhesion plaques (Crawford et al., 1994, J. Cell Biol. 124:117–127; Sadler et al., J. Cell Biol. 119:1573–1587). Moreover, h-SmLIM localizes to chromosome 3 (FIG. 3), whereas h-CRP localizes to chromosome 1 (Wang et al., 1992, Genomics 14:391–397). Finally, Northern analysis of r-CRP tissue distribution showed that the size of its mRNA and pattern of expression were distinct from those of r-SmLIM. Taken together, these data indicate that SmLIM and CRP are distinct LIM proteins.

Cellular and Chromosomal Localization of SmLIM

Figure 2A:
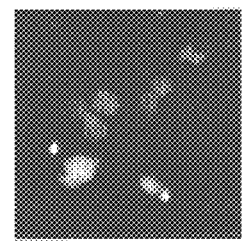
FIG. 2A is a photomicrograph of labeled cells. Cells immunostained with an anti-c-myc antibody were counterstained with Hoechst 33258 to label the nuclei. Magnification, 600×.
Figure 2B:
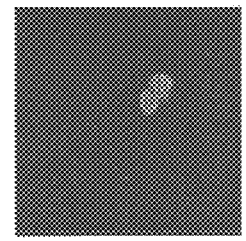
FIG. 2B is a photomicrograph of labeled cells showing the cellular localization of r-SmLIM. COS cells were transiently transfected with the c-myc-r-SmLIM hybrid construct or vector alone. Protein expression was assayed 48 h after transfection with an anti-c-myc monoclonal antibody (9E10) followed by rhodamine-conjugated secondary antibody. Magnification, 600×.
Figure 3:
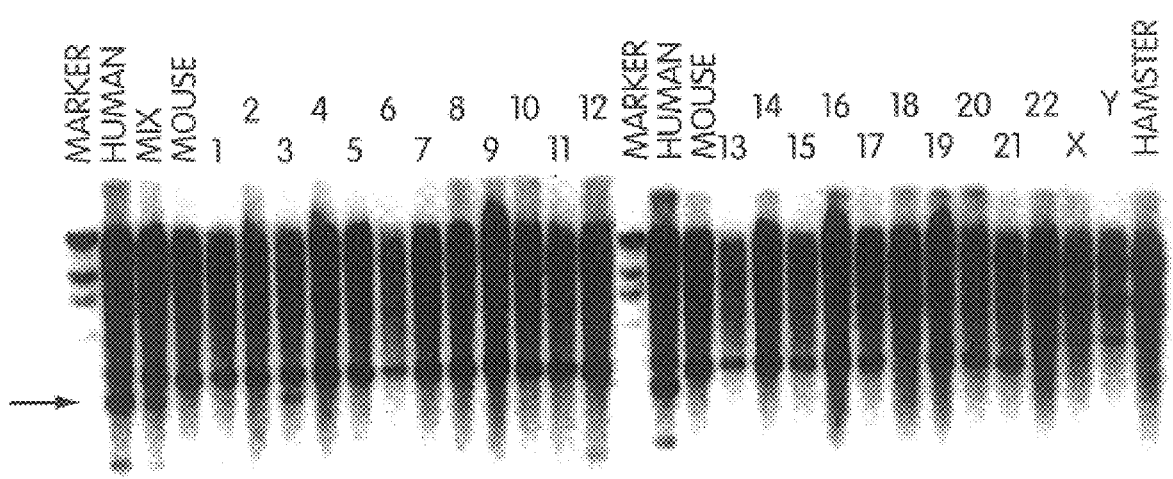
FIG. 3 is a photograph of a Southern blot assay showing chromosomal localization of human (h)-SmLIM. Individual chromosomes are numbered 1–22, X, and Y. The three control DNA samples (human, mouse, and hamster) were provided by the manufacturer of the kit (BIOS Somatic Cell Hybrid Blot). Arrow indicates specific signal for h-SmLIM visible only in the human, mix, and chromosome 3 lanes.

The r-SmLIM deduced amino acid sequence contains the putative nuclear localization signal KKYGPK (SEQ ID NO:15), suggesting that SmLIM is a nuclear protein. To determine the cellular localization of SmLIM, a plasmid expressing a fusion protein of the c-myc tag and r-SmLIM was made. This plasmid and the control vector alone were transfected into COS cells. The cells were immunostained with an anti-c-myc antibody. Detection of the immunofluorescent signal in the nuclei of COS cells transfected with the c-myc-r-SmLIM fusion plasmid but not the control vector alone indicated that the SmLIM protein localized to the nucleus (FIGS. 2A and 2B). The same experiment was performed with 10T1/2 fibroblasts. SmLIM localized to the nucleus in these cells as well. The chromosomal location of h-SmLIM was mapped with the BIOS Somatic Cell Hybrid Blot. h-SmLIM was found to localize to chromosome 3 (FIG. 3, arrow).

Tissue Distribution of r-SmLIM and h-SmLIM

Figure 4A:
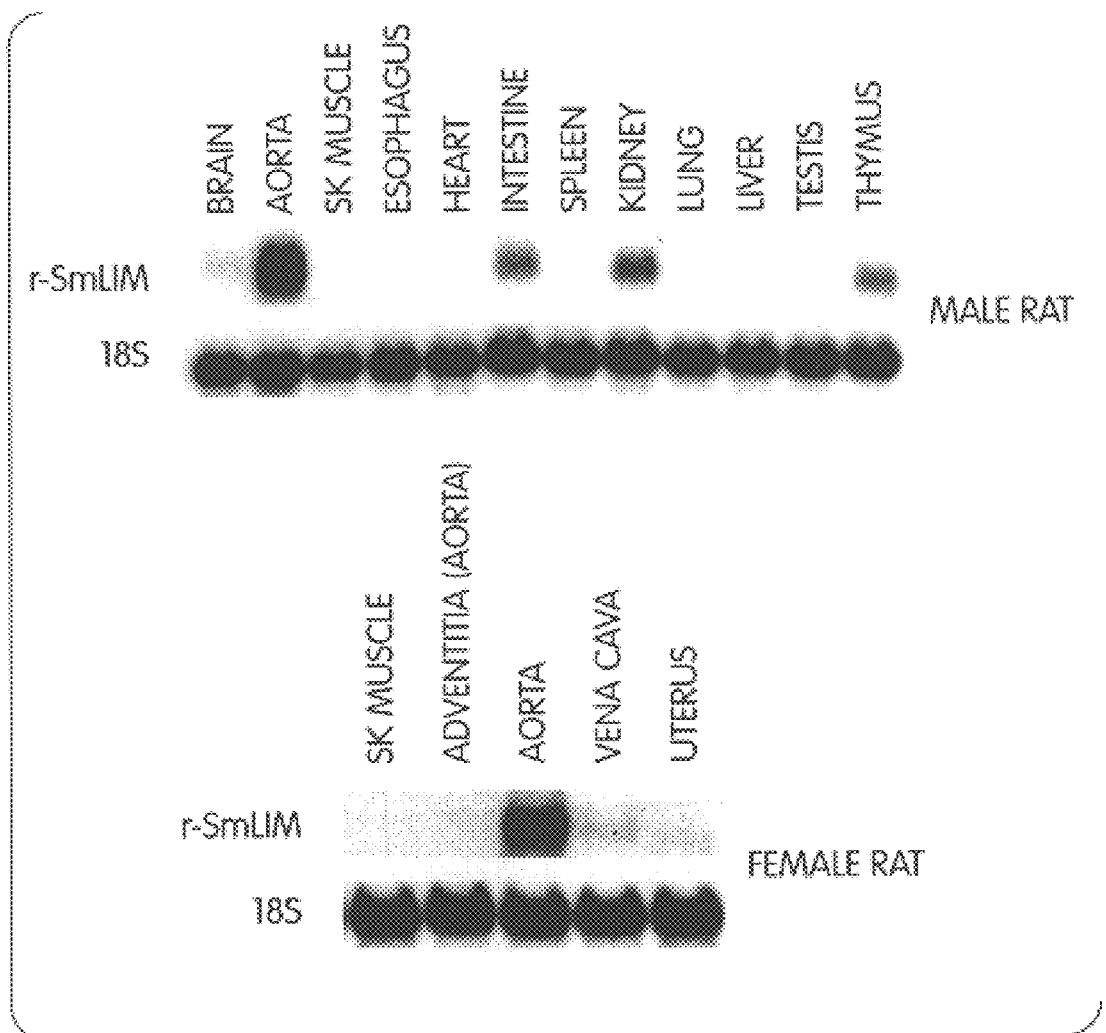
FIG. 4A is a photograph of a Northern blot assay showing r-SmLIM mRNA expression in male and female rat tissues. Northern analysis was performed with 10 μg of total RNA per lane. After electrophoresis, RNA was transferred to nitrocellulose filters and hybridized with a $^{32}$P-labeled r-SmLIM probe. A single r-SmLIM transcript is visible at 1.0 kb. Filters were hybridized with an 18S-specific probe to verify equivalent loading.
Figure 4B:
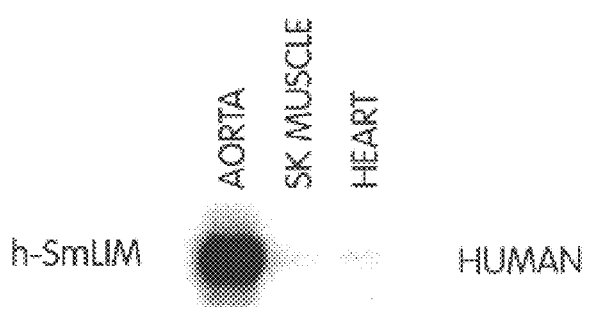
FIG. 4B is a photograph of a Northern blot assay showing h-SmLIM mRNA expression. Northern analysis was performed with 2 μg of poly A+ RNA (Clontech). A 2.1-kb transcript is shown.

Total RNA were isolated from 15 types of tissue from adult male and female rats and analyzed for SmLIM expression by Northern blot analysis (FIG. 4A). A single, intense, 1.0-kb band was detected in the aorta. A much weaker signal was detected in the kidney, thymus, and intestine. SmLIM expression was not detectable in heart and skeletal muscle and was barely detectable in brain, testis, esophagus, lung, liver, aortic adventitia, vena cava, and uterus. These data indicate that r-SmLIM is expressed in tissue containing smooth rather than striated muscle. Expression of SmLIM was found to be much greater in aortic tissue compared to intestinal or uterine tissue, indicating that SmLIM is expressed preferentially in vascular smooth muscle cells. Even among vascular RNAs, r-SmLIM expression was greater in arterial tissue (aorta) compared to venous tissue (vena cava). Consistent with the r-SmLIM expression pattern, h-SmLIM was expressed to a high degree in aorta but not in heart or skeletal muscle (FIG. 4B). The pattern of preferential expression in arterial but not venous smooth muscle cells suggests that smooth muscle cells may be fundamentally different in the two tissue types.

Although SmLIM is highly expressed in smooth muscle cells, it is not expressed in striated muscle cells (FIGS. 4A and 4B). This pattern is in contrast with that of MLP, which is expressed only in the heart and skeletal muscle. When a full-length MLP probe was hybridized to total RNA from aorta and cultured vascular smooth muscle cells, no message was detected. Thus, the expression of the two LIM proteins is distinct within the myogenic cell lineage.

Tissue Distribution of r-SmLIM (In Situ Hybridization)

Figure 5A:
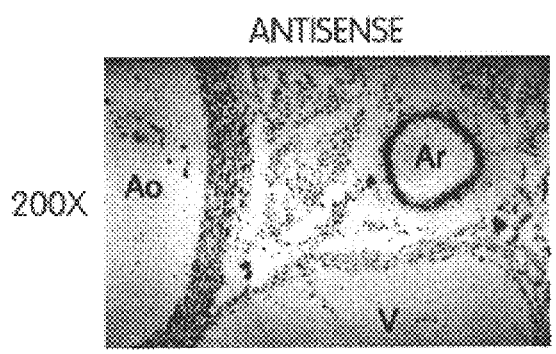
FIG. 5A is a photomicrograph of cells showing in situ hybridization of a r-SmLIM antisense probe to aorta (Ao), small artery (Ar), and vein (V) tissue sections at low magnification (200×).
Figure 5B:
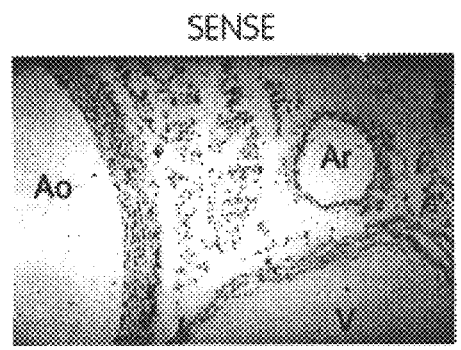
FIG. 5B is photomicrograph of cells showing in situ hybridization of a r-SmLIM sense probe to Ao, Ar, V tissue sections at low magnification (200×).
Figure 5C:
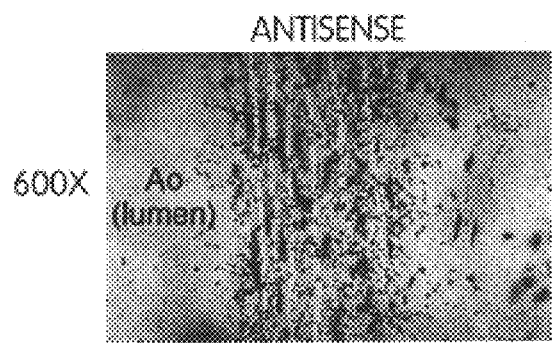
FIG. 5C is photomicrograph of cells showing in situ hybridization of a r-SmLIM antisense probe to Ao tissue at high magnification (600×).
Figure 5D:
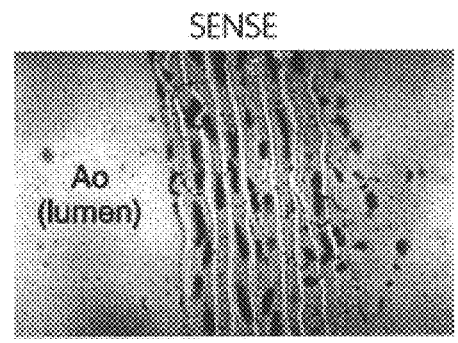
FIG. 5D is photomicrograph of cells showing in situ hybridization of a r-SmLIM sense probe to Ao tissue at high magnification (600×).

To localize r-SmLIM expression within the vessel wall, in situ hybridization was carried out. For each antisense experiment with the r-SmLIM riboprobe (FIGS. 5A and 5C), a corresponding sense (control) experiment (FIGS. 5B and 5D) was performed. FIG. 5A shows intense staining of r-SmLIM in both the aorta (Ao) and a small artery (Ar) nearby. Consistent with Northern analysis data, minimal expression of r-SmLIM was visible in the vena cava (V). A view of the aorta at higher magnification revealed that r-SmLIM expression was limited to smooth muscle cells in the medial layer (FIG. 5C). SmLIM signal expression was absent in skeletal muscle cells. These data indicate that r-SmLIM is expressed preferentially in arterial smooth muscle cells.

Figure 6A:
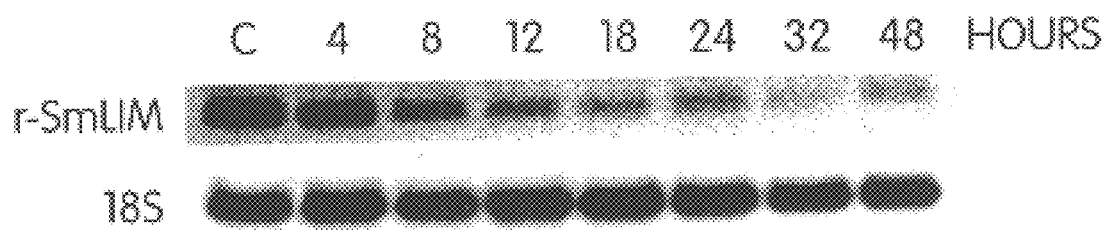
FIG. 6A is a photograph of a Northern blot assay showing a decrease in r-SmLIM mRNA expression in response to platelet derived growth factor-BB (PDGF-BB) treatment. Rat aortic smooth muscle cells were made quiescent by incubation in low-serum medium (DME plus 0.4% calf serum) for 48 h. Cells were then treated for the indicated times with PDGF-BB (20 ng/ml). Northern analysis was performed with 10 μg of total RNA per lane. After electrophoresis, RNA was transferred to nitrocellulose filters and hybridized with a $^{32}$P-labeled r-SmLIM probe. A single r-SmLIM transcript is visible at 1.0 kb. Filters were hybridized with an 18S-specific probe to verify equivalent sample loading.

Downregulation of r-SmLIM Expression in Vascular Smooth Muscle Cells by Growth Factors and Arterial Wall Injury PDGF-BB is unique among the smooth muscle cell mitogens in its ability to selectively suppress the expression of differentiation markers such as α-actin, smooth muscle myosin heavy chain, and α-tropomyosin in vitro. The effect of PDGF-BB on SmLIM expression was evaluated in cultured vascular smooth muscle cells. r-SmLIM mRNA levels decreased gradually in response to PDGF-BB stimulation (FIG. 6A). A decrease in r-SmLIM expression appeared as early as 4 h after treatment, and a maximal decrease of 80% was obtained at 32 h after treatment.

Figure 6B:
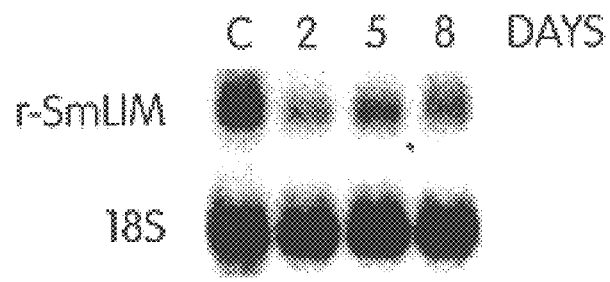
FIG. 6B is a photograph of a Northern blot assay showing a decrease in r-SmLIM mRNA expression after balloon injury in rat carotid arteries. Northern analysis was performed with 20 μg of total RNA per lane at 2, 5, and 8 days after injury. A single r-SmLIM transcript is visible at 1.0 kb. Filters were hybridized with an 18S-specific probe to verify equivalent sample loading.

In response to vessel wall injury, vascular smooth muscle cells undergo a phenotypic change from a differentiated, contractile state to a dedifferentiated, proliferative state. Balloon injury of the rat carotid artery was used to study this change in phenotype in vivo. Since smooth muscle cell proliferation after arterial injury reaches a maximum in the medial layer at 48 h and a maximum in the intimal layer at 96 h (and declines thereafter), r-SmLIM mRNA levels were evaluated at 2, 5, and 8 days after balloon injury of the carotid artery (FIG. 6B). SmLIM mRNA levels decreased by more than 60% after day 2 compared to the control, and remained at this level through day 8. These data indicate that r-SmLIM mRNA decreases in response to smooth muscle cell proliferation and dedifferentiation both in vitro and in vivo.

Developmental Regulation of r-SmLIM mRNA Expression

Figure 7A:
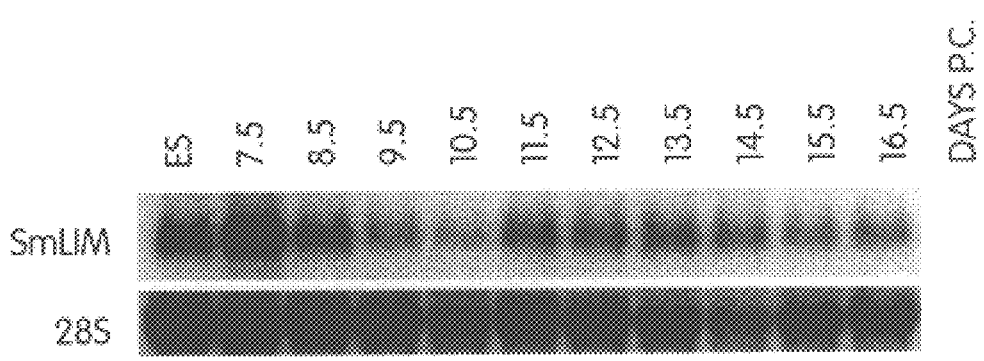
FIG. 7A is a photograph of a Northern blot assay showing expression of r-SmLIM. Total RNA isolated from undifferentiated embryonic stem cells (ES) and mouse embryos from days 7.5–16.5 post coitum (p.c.). Northern analysis was performed with 10 μg of total RNA per lane. After electrophoresis, RNA was transferred to nitrocellulose filters and hybridized with a $^{32}$P-labeled r-SmLIM probe. A single r-SmLIM transcript is visible at 1.0 kb. Filters were hybridized with a 18S ribosomal probe to verify equivalent sample loading.
Figure 7B:
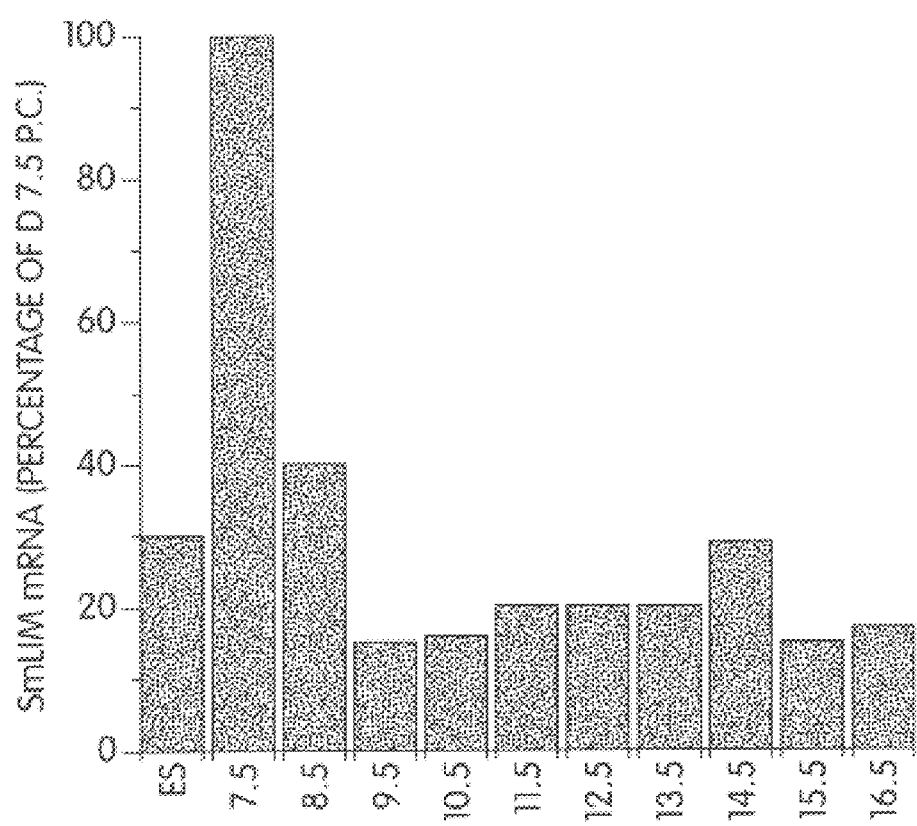
FIG. 7B is a bar graph showing the developmental regulation of SmLIM mRNA expression. The results of the Northern blot assay shown in FIG. 7A are graphically represented. The filters from the Northern blot assay were scanned to quantify the radioactivity.

SmLIM was found to be expressed preferentially in vascular tissue, and its levels are affected by the differentiation state of vascular smooth muscle cells. To determine whether SmLIM expression is regulated during development, total RNA was isolated from undifferentiated embryonic stem cells and whole mouse embryos at days 7.5–16.5 post coitum. SmLIM expression was found to be regulated developmentally (FIGS. 7A and 7B). Expression was highest during the late primitive streak stage (7.5 days p.c.), the point at which the embryonic and extraembryonic circulations begin to develop. SmLIM expression decreased rapidly at subsequent time points. The data normalized to the hybridization signal value at 7.5 days p.c. (FIG. 7B). These data indicate that relative mRNA expression decreased by 40% at 8.5 days p.c. and by approximately 80% at 9.5–16.5 days p.c.

These data indicate that SmLIM expression is regulated developmentally. Expression is highest at day 7.5 p.c. in mouse embryos (FIGS. 7A and 7B) and plateaus by day 9.5 p.c. These early stages represent important points in the development of the mouse heart and vascular systems. At the late primitive streak stage (day 7.5 p.c.), discrete blood islands make their first appearance and amalgamate shortly thereafter to form the yolk sac vasculature. Within the embryo, the early formation of a vasculature is seen at 8.0 days p.c. and amalgamation of the embryonic and extraembryonic circulations at 8.5 days p.c. SmLIM expression was found to be highest in the adult aorta and correlates with the level of smooth muscle cell differentiation, and its embryonic expression is highest during periods critical for vascular development.

Deposit

A plasmid containing DNA encoding h-SmLIM (plasmid containing h-SmLIM cDNA) has been deposited with the American Type Culture Collection (ATCC) under the terms of the Budapest Treaty on the International Recognition of the Deposit of Microorganisms for the Purpose of Patent Procedure on Mar. 13, 1996, and bears the accession number 7470. Applicants' assignee, President and Fellows of Harvard College, acknowledges its duty to replace the deposit should the depository be unable to furnish a sample when requested due to the condition of the deposit before the end of the term of a patent issued hereon, and its responsibility to notify the ATCC of the issuance of such a patent, at which time the deposit will be made available to the public. Prior to that time, the deposit will be made available to the Commissioner of Patents under the terms of CFR §1.14 and 35 U.S.C. §112.

Methods of Therapy

The invention is based on the identification and characterization of a SmLIM polypeptide which is expressed preferentially in aortic smooth muscle cells. In vivo, SmLIM mRNA levels were found to decrease as vascular smooth muscle cells changed from a quiescent to a proliferative phenotype in response to vascular injury. Thus, administering SmLIM polypeptide or increasing expression of a SmLIM-encoding DNA, e.g., by stimulating the SmLIM promoter or by introducing additional copies of SmLIM-encoding DNA, in vascular smooth muscle cells which are injured or at risk of being injured can inhibit proliferation by promoting a quiescent, differentiated state.

An animal, e.g., a human patient, with arteriosclerosis or at risk of developing arteriosclerosis (and therefore in need of inhibition of arteriosclerosis or inhibition of vascular smooth muscle cell proliferation) may be identified using standard medical procedures, such as angiographic visualization of the lumen of a blood vessel, Doppler probes for measuring velocity and volume of blood flow, stress test, and ultrasound to detect arteriosclerotic plaques. Other patients in need of inhibition of arteriosclerosis or vascular smooth muscle cell proliferation are those with angina or stroke. Improvement of the patient's condition during and after therapy may be similarly monitored. Patients undergoing invasive vascular procedures, in particular balloon angioplasty, are also at risk for developing arteriosclerosis.

Angioplasty, used to treat arteriosclerosis, involves the insertion of catheters, e.g., balloon catheters, through an occluded region of a blood vessel in order to expand the lumenal opening. However, the aftermath of angioplasty may be problematic. Restenosis, or closing of the vessel, can occur as a consequence of injury, e.g., mechanical abrasion associated with the angioplasty treatment. This restenosis is believed to be caused by proliferation of smooth muscle cells stimulated by vascular injury. Other anatomical disruptions or mechanical disturbances of a blood vessel, e.g., attributable to laser angioplasty, coronary artery surgery, atherectomy and coronary artery stents, may also cause vascular injury and subsequent proliferation of smooth muscle cells. A SmLIM polypeptide, DNA encoding a SmLIM polypeptide, or compositions which stimulate expression from be administered to increase the level of SmLIM polypeptide in the injured vascular tissue and thus inhibit the proliferation of smooth muscle cells.

SmLIM polypeptides may be administered to the patient intravenously in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 $\mu$moles of the polypeptide of the invention would be administered per kg of body weight per day. The compositions of the invention are useful for parenteral administration, such as intravenous, subcutaneous, intramuscular, and intraperitoneal routes.

DNA (e.g., SmLIM-encoding DNA, vascular cell-specific promoters, and vectors) of the invention may be introduced into target cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others. For example, the DNA of the invention under the control of a strong constitutive promoter may be administered locally to a blood vessel during balloon angioplasty using an adenovirus delivery system.

A vascular cell-specific promoter may be used to direct the expression of SmLIM or genes other than SmLIM. Thus, vascular diseases may be treated by administering a vascular cell-specific promoter of the invention operatively linked to a sequence encoding a heterologous polypeptide, e.g., a SmLIM promoter linked to DNA encoding a growth inhibitor gene such as Rb, p21 or p18.

The DNA of the invention may be administered in a pharmaceutically acceptable carrier. The therapeutic composition may also include a gene delivery system as described above. Pharmaceutically acceptable carriers are biologically compatible vehicles which are suitable for administration to an animal, e.g., physiological saline. A therapeutically effective amount is an amount of the nucleic acid of the invention which is capable of producing a medically desirable result in a treated animal.

The preferred form of the composition to be administered depends on the intended mode of administration and therapeutic application. For example, SmLIM polypeptides or SmLIM-encoding DNA may be administered in solution form through a catheter port or as a coating on the surface of a catheter, e.g., the balloon portion of a catheter used for balloon angioplasty.

As is well known in the medical arts, dosage for any given patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule. Determination of optimal dosage is well within the abilities of a pharmacologist of ordinary skill.

Drugs which stimulate the SmLIM promoter may also be administered as described above to increase the level of expression of SmLIM in vascular tissue, e.g., arterial smooth muscle cells. Such drugs can be identified by contacting the SmLIM promoter linked to a reporter gene with a candidate compound and measuring the level of expression of the reporter gene in the presence and absence of the compound. An increased level of expression in the presence of the compound compared to that in its absence indicates that the compound stimulates the SmLIM promoter.

Methods of Diagnosis

The invention includes a method of detecting injury in a sample of vascular tissue. A depressed level of SmLIM polypeptide or transcript compared to the level in normal control vascular cells would predict a high degree of smooth muscle cell proliferation indicative of vascular tissue injury, e.g., restenosis. The diagnostic method of the invention is carried out by determining the level of SmLIM gene expression in a tissue, e.g, a vascular biopsy obtained at atherectomy. The level of gene expression may be measured using methods known in the art, e.g., in situ hybridization, Northern blot analysis, or Western blot analysis using SmLIM-specific monoclonal or polyclonal antibodies. A decrease in the level of SmLIM expression in the test sample of tissue compared to the level per cell in uninjured control vascular tissue indicates the presence of a vascular injury in the test sample. It also indicates that the patient is a candidate for treatment with a therapeutic agent which increases the amount of SmLIM in the affected vascular smooth muscle cells. For example, tissue obtained at atherectomy could be tested for SmLIM expression, e.g., the level of SmLIM transcript or polypeptide. A depressed level of SmLIM transcript or polypeptide (compared to normal tissue) correlates with a high degree of smooth muscle cell proliferation indicating a high probability of restenosis. Such diagnostic procedures are useful to identify patients in need of therapeutic intervention to reduce or prevent restenosis.

Cells and Antibodies

Cells are transfected with the SmLIM-encoding DNA using standard methods. Cells, e.g, vascular smooth muscle cells, expressing a SmLIM polypeptide, may be administered to an animal locally or systemically using intravenous, subcutaneous, intramuscular, and intraperitoneal delivery methods.

Alternatively, procaryotic or eucaryotic cells in culture can be transfected with the DNA of the invention operatively linked to expression control sequences appropriate for high-level expression in the cell. Such cells are useful for producing large amounts of the SmLIM polypeptide, which can be purified and used, e.g., as a therapeutic or for raising anti-SmLIM antibodies.

The anti-SmLIM antibodies useful in the present invention can be obtained by techniques well known in the art. Such antibodies can be polyclonal or monoclonal. Polyclonal antibodies can be obtained, for example, by the methods described in Ghose et al., Methods in Enzymology, Vol. 93, 326–327, 1983. For example, a SmLIM polypeptide, or an antigenic fragment thereof, can be used as the immunogen to stimulate the production of SmLIM-reactive polyclonal antibodies in the antisera of animals such as rabbits, goats, sheep, rodents and the like.

The monoclonal antibodies useful in the present invention can be obtained by the process described by Milstein and Kohler in Nature, 256:495–97, 1975, or as modified by Gerhard, Monoclonal Antibodies, Plenum Press, 1980, pages 370–371. Hybridomas are screened to identify those producing antibodies that are highly specific for a SmLIM polypeptide. Preferably, the antibody will have an affinity of at least about $10^8$ liters/mole and more preferably, an affinity of at least about $10^9$ liters/mole. The use of such monoclonal antibodies provides a means of obtaining greater sensitivity in the assays of the present invention compared with the use of polyclonal antibodies.

Other embodiments are within the claims.

What is claimed is:

1. A substantially pure human smooth muscle cell LIM domain (SmLIM) polypeptide, that inhibits arterial smooth muscle cell proliferation, wherein the amino acid sequence of said polypeptide has at least 99% sequence identity to SEQ ID NO: 1.

2. The polypeptide of claim 1, wherein the amino acid sequence of said polypeptide comprises SEQ ID NO:1.

3. "The polypeptide of claim 1, wherein the amino acid sequence of said polypeptide consists of SEQ ID NO:1".

* * * * *

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
      (A) LENGTH: 193 amino acids
      (B) TYPE: amino acid
      (D) TOPOLOGY: linear (ii) MOLECULE TYPE: protein (xi) SEQUENCE DESCRIPTION: SEQ ID NO:1:

```
Met Pro Val Trp Gly Gly Gly Asn Lys Cys Gly Ala Cys Gly Arg Thr
 1               5                  10                  15

Val Tyr His Ala Glu Glu Val Gln Cys Asp Gly Arg Ser Phe His Arg
            20                  25                  30

Cys Cys Phe Leu Cys Met Val Cys Arg Lys Asn Leu Asp Ser Thr Thr
        35                  40                  45

Val Ala Ile His Asp Glu Glu Ile Tyr Cys Lys Ser Cys Tyr Gly Lys
    50                  55                  60

Lys Tyr Gly Pro Lys Gly Tyr Gly Tyr Gly Gln Gly Ala Gly Thr Leu
 65                  70                  75                  80

Asn Met Asp Arg Gly Glu Arg Leu Gly Ile Lys Pro Glu Ser Val Gln
                85                  90                  95

Pro His Arg Pro Thr Thr Asn Pro Asn Thr Ser Lys Phe Ala Gln Lys
            100                 105                 110

Tyr Gly Gly Ala Glu Lys Cys Ser Arg Cys Gly Asp Ser Val Tyr Ala
        115                 120                 125

Ala Glu Lys Ile Ile Gly Ala Gly Lys Pro Trp His Lys Asn Cys Phe
    130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175

Pro Lys Gly Phe Gly Tyr Gly Gln Gly Ala Gly Ala Lys Val His Ala
            180                 185                 190

Gln
```

(2) INFORMATION FOR SEQ ID NO:2:

(i) SEQUENCE CHARACTERISTICS:
      (A) LENGTH: 741 base pairs
      (B) TYPE: nucleic acid
      (C) STRANDEDNESS: both
      (D) TOPOLOGY: linear (ii) MOLECULE TYPE: DNA (xi) SEQUENCE DESCRIPTION: SEQ ID NO:2:

-continued

```
ATGCCTGTCT GGGGAGGTGG AAACAAGTGT GGGGCCTGTG GGAGGACCGT GTACCACGCA      60

GAAGAGGTGC AGTGTGATGG CAGGAGCTTC CACCGCTGCT GCTTTCTCTG CATGGTTTGC     120

AGGAAAAATT TAGATAGCAC AACAGTGGCA ATTCACGATG AAGAGATCTA CTGCAAATCC     180

TGCTACGGAA AGAAGTATGG GCCAAAAGGC TACGGTTATG GCCAGGGCGC TGGCACGCTT     240

AACATGGACC GTGGCGAGAG GCTGGGCATC AAACCAGAGA GTGTTCAGCC TCACAGGCCT     300

ACAACAAATC CAAACACTTC TAAATTTGCT CAGAAATATG GAGGTGCTGA GAAGTGTTCC     360

AGATGTGGGG ATTCTGTATA TGCTGCCGAG AAGATAATTG GAGCTGGAAA GCCCTGGCAC     420

AAAAACTGTT TCCGATGTGC AAAGTGTGGG AAGAGTCTTG AATCAACAAC TCTGACTGAA     480

AAAGAAGGTG AAATCTATTG TAAAGGATGC TATGCAAAGA ACTTTGGGCC CAAGGGATTT     540

GGCTATGGCC AAGGAGCAGG GGCTCTTGTT CATGCCCAGT AAGATGTAAA CCCTGAACTA     600

AACATCACAC ACTGAGAATC TCTTCATAAT CTAGGCACAG ATAATCTTTA ACCCGGAATT     660

CCGCCGATAC TGACGGGCTC CAGGAGTCGT CGCCACCAAG CCGAATTCCA GCACACTGGC     720

GGCCGTTACT AGTGGATCCG A                                               741
```

(2) INFORMATION FOR SEQ ID NO:3:

(i) SEQUENCE CHARACTERISTICS:
        (A) LENGTH: 427 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:3:

```
TGAGGAATGC AGCTCTTTCG CGACAGGAAA GCTGCGGATT CCAGAAGCCG GGATTCTGAC      60

CAGAGACTAT CTGCACCGGG GAGTCCTGCA CCCCGAGCTA ACATATGGCG TTTGTGCAGT     120

AAAAGGGTGG CGGGAATCCC ACGGGCGAC ACCGGATCTC GCTGGCTCCG GGCCGATCCT      180

GAGTGCTCCG GACGTCCCGG GACCGCGGGT AGGAGCAGCC GAGACGTGGG AGACTCGGAC     240

GCGGGAAGCC GCAGGAAGAG GCGGATTCCG GTCTTTTTGT CTCGGGGCCA GAGCACGAAA     300

CCCGCATCGG ATCCCCGAGC TCACGCCGGG CGGAGACCAT CGCACACCCG AGGGGCATGA     360

CCGATGGCTG AGTCGGAACA AGCCACGCCC AACATAAGTC TTTAAAAGCG GGCACACGCG     420

TCCCGCC                                                               427
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
GAGTCTTCAC CATGCCGAAC                                                  20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CTCTCCCACC CCAAAAATAG                                                      20

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:6:

Glu Gln Lys Leu Ile Ser Glu Glu Asp
 1               5

(2) INFORMATION FOR SEQ ID NO:7:

(i) SEQUENCE CHARACTERISTICS:
        (A) LENGTH: 880 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: Coding Sequence
        (B) LOCATION: 55...633

(xi) SEQUENCE DESCRIPTION: SEQ ID NO:7:

```
ACGAGCTAGA CCTCCCTAGC TCCGCCCGCC GCGTGCTCCC GCCTCCCACT CGGA ATG           57
                                                          Met
                                                           1

CCT GTC TGG GGG GGT GGA AAT AAG TGC GGG GCC TGC GGG AGA ACC GTG          105
Pro Val Trp Gly Gly Gly Asn Lys Cys Gly Ala Cys Gly Arg Thr Val
         5                  10                 15

TAC CAC GCT GAA GAG GTG CAG TGT GAT GGG CGG ACG TTC CAC CGC TGC          153
Tyr His Ala Glu Glu Val Gln Cys Asp Gly Arg Thr Phe His Arg Cys
             20                 25                 30

TGC TTT CTG TGC ATG GTT TGC AGG AAA AAT TTA GAC AGC ACA ACA GTG          201
Cys Phe Leu Cys Met Val Cys Arg Lys Asn Leu Asp Ser Thr Thr Val
         35                 40                 45

GCA ATT CAT GAT GAA GAG ATC TAC TGC AAA TCA TGC TAC GGA AAG AAG          249
Ala Ile His Asp Glu Glu Ile Tyr Cys Lys Ser Cys Tyr Gly Lys Lys
 50              55                 60                 65

TAT GGA CCA AAA GGC TAT GGT TAT GGC CAG GGC GCT GGC ACG CTC AAC          297
Tyr Gly Pro Lys Gly Tyr Gly Tyr Gly Gln Gly Ala Gly Thr Leu Asn
             70                 75                 80

ATG GAC CGT GGT GAG AGG CTG GGC ATC AAG CCA GAG AGT GCT CAA CCT          345
Met Asp Arg Gly Glu Arg Leu Gly Ile Lys Pro Glu Ser Ala Gln Pro
             85                 90                 95

CAC AGG CCT ACA ACA AAT CCA AAC ACT TCT AAA TTT GCC CAG AAA TAT          393
His Arg Pro Thr Thr Asn Pro Asn Thr Ser Lys Phe Ala Gln Lys Tyr
         100                105                110

GGA GGT GCT GAG AAG TGC TCC AGA TGT GGG GAT TCT GTG TAT GCT GCT          441
Gly Gly Ala Glu Lys Cys Ser Arg Cys Gly Asp Ser Val Tyr Ala Ala
     115                120                125

GAG AAG ATC ATT GGA GCT GGA AAG CCC TGG CAC AAA AAC TGT TTC CGA          489
Glu Lys Ile Ile Gly Ala Gly Lys Pro Trp His Lys Asn Cys Phe Arg
130              135                140                145
```

```
TGT GCC AAG TGT GGG AAG AGT CTG GAG TCT ACA ACT CTG ACT GAG AAG    537
Cys Ala Lys Cys Gly Lys Ser Leu Glu Ser Thr Thr Leu Thr Glu Lys
            150                 155                 160

GAA GGT GAA ATC TAC TGT AAA GGG TGC TAC GCA AAG AAC TTT GGG CCC    585
Glu Gly Glu Ile Tyr Cys Lys Gly Cys Tyr Ala Lys Asn Phe Gly Pro
        165                 170                 175

AAG GGA TTC GGC TAT GGT CAA GGA GCA GGG GCC CTT GTT CAT GCT CAG    633
Lys Gly Phe Gly Tyr Gly Gln Gly Ala Gly Ala Leu Val His Ala Gln
            180                 185                 190

TAGTGGTGTA AACCCAGTAA GCATGGCAAA GAACCTCCAT TAATGTGGAT GGCCTTACCG    693

CACTCAGGCT GTGCATCGGC CAGCACTCAG CACTGTGTAG CACACACGCT ATGTGCACAA    753

TCGGGCTGGA CAGGAAGCAC TACACTCTCC TGCCCATCCG CTAACGTTTA AGAACGTTCT    813

TTTACATTTG GAATAAAATT TTGGTTTGAT TGAAAAAAA AAAAAAAAAA AAAAAAAAA     873

AAAAAAA                                                             880
```

(2) INFORMATION FOR SEQ ID NO:8:

(i) SEQUENCE CHARACTERISTICS:
        (A) LENGTH: 193 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:8:

```
Met Pro Val Trp Gly Gly Gly Asn Lys Cys Gly Ala Cys Gly Arg Thr
 1               5                  10                  15

Val Tyr His Ala Glu Glu Val Gln Cys Asp Gly Arg Thr Phe His Arg
                20                  25                  30

Cys Cys Phe Leu Cys Met Val Cys Arg Lys Asn Leu Asp Ser Thr Thr
            35                  40                  45

Val Ala Ile His Asp Glu Glu Ile Tyr Cys Lys Ser Cys Tyr Gly Lys
        50                  55                  60

Lys Tyr Gly Pro Lys Gly Tyr Gly Tyr Gly Gln Gly Ala Gly Thr Leu
65                  70                  75                  80

Asn Met Asp Arg Gly Glu Arg Leu Gly Ile Lys Pro Glu Ser Ala Gln
                85                  90                  95

Pro His Arg Pro Thr Thr Asn Pro Asn Thr Ser Lys Phe Ala Gln Lys
            100                 105                 110

Tyr Gly Gly Ala Glu Lys Cys Ser Arg Cys Gly Asp Ser Val Tyr Ala
        115                 120                 125

Ala Glu Lys Ile Ile Gly Ala Gly Lys Pro Trp His Lys Asn Cys Phe
    130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175

Pro Lys Gly Phe Gly Tyr Gly Gln Gly Ala Gly Ala Leu Val His Ala
            180                 185                 190

Gln
```

(2) INFORMATION FOR SEQ ID NO:9:

(i) SEQUENCE CHARACTERISTICS:
        (A) LENGTH: 193 amino acids (B) TYPE: amino acid
            (D) TOPOLOGY: linear (ii) MOLECULE TYPE: protein (xi) SEQUENCE DESCRIPTION: SEQ ID NO:9:

Met Pro Asn Trp Gly Gly Gly Lys Lys Cys Gly Val Cys Gln Lys Thr
  1               5                  10                  15

Val Tyr Phe Ala Glu Glu Val Gln Cys Glu Gly Asn Ser Phe His Lys
                 20                  25                  30

Ser Cys Phe Leu Cys Met Val Cys Lys Lys Asn Leu Asp Ser Thr Thr
             35                  40                  45

Val Ala Val His Gly Glu Glu Ile Tyr Cys Lys Ser Cys Tyr Gly Lys
         50                  55                  60

Lys Tyr Gly Pro Lys Gly Tyr Gly Tyr Gly Gln Gly Ala Gly Thr Leu
 65                  70                  75                  80

Ser Met Asp Lys Gly Glu Ser Leu Gly Ile Lys His Glu Glu Ala Pro
                 85                  90                  95

Gly His Arg Pro Thr Thr Asn Pro Asn Ala Ser Lys Phe Ala Gln Lys
                100                 105                 110

Ile Gly Gly Ser Glu Arg Cys Pro Arg Cys Ser Gln Ala Val Tyr Ala
            115                 120                 125

Ala Glu Lys Val Ile Gly Ala Gly Lys Ser Trp His Lys Ser Cys Phe
        130                 135                 140

Arg Cys Ala Lys Cys Gly Lys Gly Leu Glu Ser Thr Thr Leu Ala Asp
145                 150                 155                 160

Lys Asp Gly Glu Ile Tyr Cys Lys Gly Cys Tyr Ala Lys Asn Phe Gly
                165                 170                 175

Pro Lys Gly Phe Gly Phe Gly Gln Gly Ala Gly Ala Leu Val His Ser
                180                 185                 190

Glu (2) INFORMATION FOR SEQ ID NO:10:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO:10:

Met Pro Asn Trp Gly Gly Gly Lys Lys Cys Gly Val Cys Gln Lys Thr
  1               5                  10                  15

Val Tyr Phe Ala Glu Glu Val Gln Cys Glu Gly Asn Ser Phe His Lys
                 20                  25                  30

Ser Cys Phe Leu Cys Met Val Cys Lys Lys Asn Leu Asp Ser Thr Thr
             35                  40                  45

Val Ala Val His Gly Glu Glu Ile Tyr Cys Lys Ser Cys Tyr Gly Lys
         50                  55                  60

Lys Tyr Gly Pro Lys Gly Tyr Gly Tyr Gly Gln Gly Ala Gly Thr Leu
 65                  70                  75                  80

Ser Thr Asp Lys Gly Glu Ser Leu Gly Ile Lys Gly Glu Glu Ala Pro
                 85                  90                  95

Gly His Arg Pro Thr Thr Asn Pro Asn Ala Ser Lys Phe Ala Gln Lys
                100                 105                 110

Ile Gly Gly Ser Glu Arg Cys Pro Arg Cys Ser Gln Ala Val Tyr Ala

```
                115                 120                 125
Ala Glu Lys Val Ile Gly Ala Gly Lys Ser Gln His Lys Ala Cys Phe
    130                 135                 140

Arg Cys Ala Lys Cys Gly Lys Gly Leu Glu Ser Thr Thr Leu Ala Asp
145                 150                 155                 160

Lys Asp Gly Glu Ile Tyr Cys Lys Gly Cys Tyr Ala Lys Asn Phe Gly
                165                 170                 175

Pro Lys Gly Phe Gly Phe Gly Gln Gly Ala Gly Ala Leu Val His Ser
                180                 185                 190

Glu
```

(2) INFORMATION FOR SEQ ID NO:11:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO:11:

```
Met Pro Asn Trp Gly Gly Gly Ala Lys Cys Gly Ala Cys Asp Lys Thr
1               5                   10                  15

Val Tyr Gly Ala Glu Glu Ile Gln Cys Asn Gly Arg Ser Phe His Lys
                20                  25                  30

Thr Cys Phe His Cys Met Ala Cys Arg Lys Ala Leu Asp Ser Thr Thr
            35                  40                  45

Val Ala Ala His Glu Ser Glu Ile Tyr Cys Lys Val Cys Tyr Gly Arg
        50                  55                  60

Lys Tyr Gly Pro Lys Gly Ile Gly Phe Gly Gln Gly Ala Gly Cys Leu
65                  70                  75                  80

Ser Thr Asp Thr Gly Glu His Leu Gly Leu Gln Phe Gln Gln Ser Pro
                85                  90                  95

Lys Pro Ala Arg Ala Ala Thr Thr Ser Asn Pro Ser Lys Phe Ser Ala
            100                 105                 110

Lys Phe Gly Glu Ser Glu Lys Cys Pro Arg Cys Gly Lys Ser Val Tyr
        115                 120                 125

Ala Ala Glu Lys Val Met Gly Gly Gly Lys Pro Trp His Lys Thr Cys
    130                 135                 140

Phe Pro Cys Ala Ile Cys Gly Lys Ser Leu Glu Ser Thr Asn Val Thr
145                 150                 155                 160

Asp Lys Asp Gly Glu Leu Tyr Cys Lys Val Cys Tyr Ala Lys Asn Phe
                165                 170                 175

Gly Pro Thr Gly Ile Gly Phe Gly Gly Leu Thr His Gln Val Glu Lys
                180                 185                 190

Lys Glu
```

(2) INFORMATION FOR SEQ ID NO:12:

(i) SEQUENCE CHARACTERISTICS:
        (A) LENGTH: 194 amino acids
        (B) TYPE: amino acid
        (D) TOPOLOGY: linear (ii) MOLECULE TYPE: protein (ix) FEATURE:
        (B) LOCATION: 3, 8, 12, 14-15, 19, 26, 28-29, 32-33, 36, 39,
            41, 43, 51, 53-54, 60, 64, 71, 79, 81-82, 84, 87, 90-99, 101-102, 104-105, 107, 111-112, 114, 116-117, 119, 121,
124-126, 133-134, 136, 139, 143, 146, 149, 153, 158-161,
163, 166, 170, 179, 181, 183, 185-194
  (D) OTHER INFORMATION: where Xaa at the above positions
      is any amino acid (xi) SEQUENCE DESCRIPTION: SEQ ID NO:12:

```
Met Pro Xaa Trp Gly Gly Gly Xaa Lys Cys Gly Xaa Cys Xaa Xaa Thr
 1               5                  10                  15

Val Tyr Xaa Ala Glu Glu Val Gln Cys Xaa Gly Xaa Xaa Phe His Xaa
            20                  25                  30

Xaa Cys Phe Xaa Cys Met Xaa Cys Xaa Lys Xaa Leu Asp Ser Thr Thr
        35                  40                  45

Val Ala Xaa His Xaa Xaa Glu Ile Tyr Cys Lys Xaa Cys Tyr Gly Xaa
    50                  55                  60

Lys Tyr Gly Pro Lys Gly Xaa Gly Tyr Gly Trp Gly Ala Gly Xaa Leu
65                  70                  75                  80

Xaa Xaa Asp Xaa Gly Glu Xaa Leu Gly Xaa Xaa Xaa Xaa Xaa Xaa Xaa
            85                  90                  95

Xaa Xaa Xaa Arg Xaa Xaa Thr Xaa Xaa Asn Xaa Ser Lys Phe Xaa Xaa
        100                 105                 110

Lys Xaa Gly Xaa Xaa Glu Xaa Cys Xaa Arg Cys Xaa Xaa Xaa Val Tyr
    115                 120                 125

Ala Ala Glu Lys Xaa Xaa Gly Xaa Gly Lys Xaa Trp His Lys Xaa Cys
130                 135                 140

Phe Xaa Cys Ala Xaa Cys Gly Lys Xaa Leu Glu Ser Thr Xaa Xaa Xaa
145                 150                 155                 160

Xaa Lys Xaa Gly Glu Xaa Tyr Cys Lys Xaa Cys Tyr Ala Lys Asn Phe
            165                 170                 175

Gly Pro Xaa Gly Xaa Gly Xaa Gly Xaa Xaa Xaa Xaa Xaa Xaa Xaa
            180                 185                 190

Xaa Xaa
```

(2) INFORMATION FOR SEQ ID NO:13:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO:13:

```
Met Pro Val Trp Gly Gly Gly Asn Lys Cys Gly Ala Cys Gly Arg Thr
 1               5                  10                  15

Val Tyr His Ala Glu Glu Val Gln Cys Asp Gly Arg Thr Phe His Arg
            20                  25                  30

Cys Cys Phe Leu Cys Met Val Cys Arg Lys Asn Leu Asp Ser Thr Thr
        35                  40                  45

Val Ala Ile His Asp Glu Ile Tyr Cys Lys Ser Cys Tyr Gly Lys
    50                  55                  60

Lys Tyr Gly Pro Lys Gly Tyr Gly Tyr Gln Gly Ala Gly Thr Leu
65                  70                  75                  80

Asn Met Asp Arg Gly Glu Arg Leu Gly Ile Lys Pro Glu Ser Ala Gln
            85                  90                  95

Pro His Arg Pro Thr Thr Asn Pro Asn Thr Ser Lys Phe Ala Gln Lys
        100                 105                 110
```

Tyr Gly Gly Ala Glu Lys Cys Ser Arg Cys Gly Asp Ser Val Tyr Ala
        115                 120                 125

Ala Glu Lys Ile Ile Gly Ala Gly Lys Pro Trp His Lys Asn Cys Phe
        130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175

Pro Lys Gly Phe Gly Tyr Gly Gln Gly Ala Gly Ala Leu Val His Ala
            180                 185                 190

Gln (2) INFORMATION FOR SEQ ID NO:14:

(i) SEQUENCE CHARACTERISTICS:
        (A) LENGTH: 840 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:14:

```
AGTCTCCGGA TCCGCCCGCG GCTTTCCTCG GTCAGACCTC GTTAGCTCCG CCCGCCGCGT    60

GCTCCCTCCT CCCACTCGGA ATGCCTGTCT GGGGCGGTGG AAATAAGTGC GGGGCCTGCG   120

GGAGAACCGT GTACCACGCG GAAGAGGTGC AGTGCGATGG GCGGACGTTC CATCGCTGCT   180

GCTTCCTGTG CATGGTTTGC AGGAAAAATT TAGACAGCAC AACAGTGGCG ATTCATGATG   240

AAGAGATCTA CTGCAAATCC TGCTACGGAA AGAAGTATGG ACCAAAAGGC TATGGTTATG   300

GCCAGGGCGC TGGCACGCTC AACATGGACC GCGGTGAGAG ACTGGGCATC AAGCCAGAGA   360

GTGCTCAACC TCACAGGCCT ACGACAAATC CAAACACTTC TAAATTTGCC CAGAAATATG   420

GAGGAGCTGA GAAGTGTTCC AGGTGTGGGG ATTCCGTGTA TGCTGCGGAG AAGATCATTG   480

GAGCTGGGAA GCCCTGGCAC AAAAACTGTT TCCGGTGTGC CAAGTGTGGG AAGAGTCTGG   540

AGTCTACAAC TCTGACTGAG AAAGAAGGCG AAATCTACTG TAAAGGGTGC TACGCAAAGA   600

ACTTTGGGCC CAAGGGATTT GGCTATGGTC AAGGGGCAGG GGCCCTTGTT CATGCTCAGT   660

AATGGTGTGA ACCAGTAAGC ACGACAGAGA ATCTCCATTA CCAAACTGCA GATGGCGTTT   720

ATGGCGCTCA CTACTGTGAA ACAGCCAGCA CTTGGCACTG GCATCACCG AGCTGCCTGT   780

GGGGGCTGGA CCGACAGCGC TGCACTCTCC CGCCCACTCA CTAGCGTCTA AGAGCATTCT   840
```

(2) INFORMATION FOR SEQ ID NO:15:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:15:

Lys Lys Tyr Gly Pro Lys
  1               5

(2) INFORMATION FOR SEQ ID NO:16:

(i) SEQUENCE CHARACTERISTICS:
        (A) LENGTH: 522 base pairs
        (B) TYPE: nucleic acid (C) STRANDEDNESS: both
(D) TOPOLOGY: linear (ii) MOLECULE TYPE: DNA (xi) SEQUENCE DESCRIPTION: SEQ ID NO:16:

```
TGAGGAATGC AGCTCTTTCG CGACAGGAAA GCTGCGGATT CCAGAAGCCG GGATTCTGAC      60

CAGAGACTAT CTGCACCGGG GAGTCCTGCA CCCCGAGCTA ACATATGGCG TTTGTGCAGT     120

AAAAGGGTGG CGGGAATCCC ACGGGGCGAC ACCGGATCTC GCTGGCTCCG GGCCGATCCT     180

GAGTGCTCCG GACGTCCCGG GACCGCGGGT AGGAGCAGCC GAGACGTGGG AGACTCGGAC     240

GCGGGAAGCC GCAGGAAGAG GCGGATTCCG GTCTTTTTGT CTCGGGGCCA GAGCACGAAA     300

CCCGCATCGG ATCCCCGAGC TCACGCCGGG CGGAGACCAT CGCACACCCG AGGGGCATGA     360

CCGATGGCTG AGTCGGAACA AGCCACGCCC AACATAAGTC TTTAAAAGCG GGCACACGCG     420

TCCCGCCAGT CTCCGGATCC GCCCGCCGGC TTTCCTCGGT CAGACCTCGT TAGCTCCGCC     480

CGCCGCGTGC TCCCTCCTCC CACTCGGGTG AGTCCTAGGC TC                       522
```

(2) INFORMATION FOR SEQ ID NO:17:

(i) SEQUENCE CHARACTERISTICS:
(A) LENGTH: 297 base pairs
(B) TYPE: nucleic acid
(C) STRANDEDNESS: both
(D) TOPOLOGY: linear (ii) MOLECULE TYPE: DNA (xi) SEQUENCE DESCRIPTION: SEQ ID NO:17:

```
ATTTGGGTAC CACCTCTTAA TTAACCTTTC AGAGGAGCTG TTGTGATTTT TAGATGATGA      60

GAAGTTATCT GGTTCCTTCC TCCAGTGAAA ACCAGTCTCC TGATTAAAAA AAAAAAAAAG    120

ACCGTTTCTT TAAAAAGACA ATCAATTCCT TTATGCAGTA GGCTAACATT TGCACTCTGA    180

GAGCTGAAAA CGACATTTTA CTTTTGAGAT TTTCATTCAT ATATATATAT ATATATACAT    240

ATATATATAT ATATATATAT ATATATATAT ATATATATAT ACAAAACACT CCGTGGA       297
```

(2) INFORMATION FOR SEQ ID NO: 18:

(i) SEQUENCE CHARACTERISTICS:
(A) LENGTH: 52 amino acids
(B) TYPE: amino acid
(D) TOPOLOGY: linear (ii) MOLECULE TYPE: protein (ix) FEATURE:
(B) LOCATION: 2-3, 5-21, 23-24, 26-27, 29-30, 32-48, 50-52
(D) OTHER INFORMATION: where Xaa at the above positions is any amino acid (xi) SEQUENCE DESCRIPTION: SEQ ID NO:18:

```
Cys Xaa Xaa Cys Xaa Xaa Xaa Xaa Xaa Xaa Xaa Xaa Xaa Xaa Xaa
  1               5                  10                  15

Xaa Xaa Xaa Xaa Xaa His Xaa Xaa Cys Xaa Xaa Cys Xaa Xaa Cys Xaa
             20                  25                  30

Xaa Xaa Xaa Xaa Xaa Xaa Xaa Xaa Xaa Xaa Xaa Xaa Xaa Xaa Xaa
         35                  40                  45

Cys Xaa Xaa Xaa
         50
```

(2) INFORMATION FOR SEQ ID NO:19:

(i) SEQUENCE CHARACTERISTICS:
        (A) LENGTH: 79 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:19:

```
AGTCTCCGGA TCCGCCCGCG GCTTTCCTCG GTCAGACCTC GTTAGCTCCG CCCGCCGCGT    60

GCTCCCTCCT CCCACTCGG                                                 79
```

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:20:

```
GTGAGTCCTA GGCTC                                                     15
```

(2) INFORMATION FOR SEQ ID NO:21:

(i) SEQUENCE CHARACTERISTICS:
        (A) LENGTH: 215 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:21:

```
GAGCTCTGTG AGTAAGAGCG ATGTTTCCTC CACGATATGC TAGATAAAAA TCTGGGGGTG    60

GGGGGTAACC AGAAGAGGGA CAAAGCACCT TGTACTAATT GTTTAAATAT TTAATAAAGG   120

TCTCATCAGG AAACCTAATA GAGGTCTGCA CCATTTAATG GTTGTATGGG AATCACGCCT   180

TTAAGGCAAA GATGAGCTTT CTCTGCTACA GACTA                              215
```

(2) INFORMATION FOR SEQ ID NO:22:

(i) SEQUENCE CHARACTERISTICS:
        (A) LENGTH: 90 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:22:

```
AAGCATCTGC TAGTACGCAC TGTCTCGTGG CTGAAGCAGC CGGAGGGAAC TCGTAAAACA    60

ACGCATCCTA ATGCATCCTT TGTTCCGCAG                                     90
```

(2) INFORMATION FOR SEQ ID NO:23:

(i) SEQUENCE CHARACTERISTICS:
        (A) LENGTH: 113 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:23:

| CATGCCTGTC TGGGGCGGTG GAAATAAGTG CGGGGCCTGC GGGAGAACCG TGTACCACGC | 60 |
| GGAAGAGGTG CAGTGCGATG GGCGGACGTT CCATCGCTGC TGCTTCCTGT GCA | 113 |

(2) INFORMATION FOR SEQ ID NO:24:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:24:

```
Met Pro Val Trp Gly Gly Gly Asn Lys Cys Gly Ala Cys Gly Arg Thr
 1               5                  10                  15

Val Tyr His Ala Glu Glu Val Gln Cys Asp Gly Arg Thr Phe His Arg
            20                  25                  30

Cys Cys Phe Leu Cys Met
        35
```

(2) INFORMATION FOR SEQ ID NO:25:

(i) SEQUENCE CHARACTERISTICS:
        (A) LENGTH: 256 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:25:

| GTGAGTATGG TCCCCTCCCC CTTCAGTTCA CCTCTGGAAG AAAAATAACA ATGCTAGCTA | 60 |
| AGAGAAATGG TTTAGAGTGA CGGGGTTTTT TGTTTGTTTG TTTTTTGTTT TAACCGCTGA | 120 |
| GTCATCTCTC TAGCCCAATG CGGTGTTTTA TGTCATTGAT CTTAAGACGC TGAGGACTGA | 180 |
| GCCAGAGGGA AGACCACCTA GCCCTCAGTT CTGGCCAGTT GGCTTAGCCT TTGTCACCTC | 240 |
| TGTCTGTGTC CTCGGG | 256 |

(2) INFORMATION FOR SEQ ID NO:26:

(i) SEQUENCE CHARACTERISTICS:
        (A) LENGTH: 129 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:26:

| GTCATTTGGA GGCACCTCTG TTTTAAGTTA AAGCTATATA TATATATATA TATATATATA | 60 |
| TATATATATA TATATATATA TATATTCATA TTTTAATGAT GTTTAAAAATC TATCTACCCT | 120 |
| GGGGCTTAG | 129 |

(2) INFORMATION FOR SEQ ID NO:27:

(i) SEQUENCE CHARACTERISTICS:
        (A) LENGTH: 169 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:27:

| | | | | |
|---|---|---|---|---|
| TGGTTTGCAG GAAAAATTTA GACAGCACAA CAGTGGCGAT TCATGATGAA GAGATCTACT | | | | 60 |
| GCAAATCCTG CTACGAAAG AAGTATGGAC CAAAAGGCTA TGGTTATGGC CAGGGCGCTG | | | | 120 |
| GCACGCTCAA CATGGACCGC GGTGAGAGAC TGGGCATCAA GCCAGAGAG | | | | 169 |

(2) INFORMATION FOR SEQ ID NO:28:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:28:

Val Cys Arg Lys Asn Leu Asp Ser Thr Thr Val Ala Ile His Asp Glu
 1               5                  10                  15

Glu Ile Tyr Cys Lys Ser Cys Tyr Gly Lys Lys Tyr Gly Pro Lys Gly
             20                  25                  30

Tyr Gly Tyr Gly Gln Gly Ala Gly Thr Leu Asn Met Asp Arg Gly Glu
         35                  40                  45

Arg Leu Gly Ile Lys Pro Glu Ser
     50                  55

(2) INFORMATION FOR SEQ ID NO:29:

(i) SEQUENCE CHARACTERISTICS:
        (A) LENGTH: 448 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:29:

| | | | | |
|---|---|---|---|---|
| GTGAGAGAAT GTTACCCTCT TAAAAGCGGG TAGAACAGCT CCTGTCGCTC AGGCACCAGG | | | | 60 |
| AGCCTGCATA TTTAGTTTAA ACTAAGCAAG CAAAATAAAA TGTGACCTCT ACTAAATACT | | | | 120 |
| CATATGATTA CTACGACGTT CTGTAACGTC ATAATATTGA CAGTTTTGTA TCTAAAAATC | | | | 180 |
| TTAGTAATGA ATGCAGGGAC TTCTAGCCCT GGTTATATAG CATTTTAACT GATATCAGGA | | | | 240 |
| AAACATAAAT CTCAAGGAAC TGACTTACTT AATATCCCAT ACGCACTGGA GATCAAATAT | | | | 300 |
| CTTGAAATGA GTGTCTGAAT TCTGAGATCG TTCTCATATG ATTAACTGTC CACGGAAAGT | | | | 360 |
| CCTTAGTCAC TCTTTCCTCA GGAAATTACA TCCTTCAACT TAGAAATTAA AACCATTTCC | | | | 420 |
| TCGTTCTGAT GATTTGAGGG ACAAATCG | | | | 448 |

(2) INFORMATION FOR SEQ ID NO:30:

(i) SEQUENCE CHARACTERISTICS:
        (A) LENGTH: 306 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:30:

| | | | | |
|---|---|---|---|---|
| AAATGTTTCA CAATATACAT TACCTCTAAA TCTTCCCATC AATGAAAACT AAATTCACAA | | | | 60 |

```
GACCCCCAAG GCTGTGTTTG TAGCCAGAAC TGGGAAATCA CGGATGCTCT TTCTGCCCTG      120

TCCCCACCTT TCCCAGCAAT AAGCAAGCTC TGTGTGCACG CCCTATGTGC AGTGGTAACC      180

CTGTCTGTCC CTTCCAGCCG GGCCCTGGTC TGGTCTTCCT CTGCGATCAG GTCTAAGGAA      240

TTCCTCCTCC CAGAGGTCTT CTTTAGGACT CAAAACCATG GCCTGCCTTT AACACACAG       300

ATTAAA                                                                 306

(2) INFORMATION FOR SEQ ID NO:31:

(i) SEQUENCE CHARACTERISTICS:
        (A) LENGTH: 69 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:31:

CGAAGCTCCT GTTAGCTCAG GAGGAACATT TGGAGAAACA CTGCCTCATT TTTTTCTCCG       60

TTCCTCCAG                                                              69

(2) INFORMATION FOR SEQ ID NO:32:

(i) SEQUENCE CHARACTERISTICS:
        (A) LENGTH: 130 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:32:

TGCTCAACCT CACAGGCCTA CGACAAATCC AAACACTTCT AAATTTGCCC AGAAATATGG       60

AGGAGCTGAG AAGTGTTCCA GGTGTGGGGA TTCCGTGTAT GCTGCGGAGA AGATCATTGG      120

AGCTGGGAAG                                                             130

(2) INFORMATION FOR SEQ ID NO:33:

(i) SEQUENCE CHARACTERISTICS:
        (A) LENGTH: 43 amino acids
        (B) TYPE: amino acid
        (D) TOPOLOGY: linear (ii) MOLECULE TYPE: protein (xi) SEQUENCE DESCRIPTION: SEQ ID NO:33:

Ala Gln Pro His Arg Pro Thr Thr Asn Pro Asn Thr Ser Lys Phe Ala
 1               5                  10                  15

Gln Lys Tyr Gly Gly Ala Glu Lys Cys Ser Arg Cys Gly Asp Ser Val
            20                  25                  30

Tyr Ala Ala Glu Lys Ile Ile Gly Ala Gly Lys
            35                  40

(2) INFORMATION FOR SEQ ID NO:34:

(i) SEQUENCE CHARACTERISTICS:
        (A) LENGTH: 142 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:34:
```

```
GTAGGGCGCT GTCTCTAAGT GGTAACTGCA GCACACACTC ACACACACAC AGGGTGCTGT      60

CTGTCTCTAA CTGGTAACTG TAATAAACAC ACACATACAT ACACAAGCAT ACATAGACAC     120

ACACACACAC ACACACACAT AC                                              142
```

(2) INFORMATION FOR SEQ ID NO:35:

(i) SEQUENCE CHARACTERISTICS:
        (A) LENGTH: 188 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:35:

```
CTGCTCCCAG CAAACAGCCC TTTACTGGTG GCTAGAAGAT ATGACAGCAA AGAGGCCAGC      60

TTTCTAGCTG AGCCAAACCG TAGCCTGAGG AGGCTGCTTG TGCGCTGGTT TTCCCAGCCA     120

CTTGCTGCAT CTAGATCGAG CCAAAGGAAA CAAGCCTCTC AATGTCCTAA CTCAGCTGTC     180

TCTTCCAG                                                              188
```

(2) INFORMATION FOR SEQ ID NO:36:

(i) SEQUENCE CHARACTERISTICS:
        (A) LENGTH: 94 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:36:

```
CCCTGGCACA AAAACTGTTT CCGGTGTGCC AAGTGTGGGA AGAGTCTGGA GTCTACAACT      60

CTGACTGAGA AAGAAGGCGA AATCTACTGT AAAG                                  94
```

(2) INFORMATION FOR SEQ ID NO:37:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:37:

```
Pro Trp His Lys Asn Cys Phe Arg Cys Ala Lys Cys Gly Lys Ser Leu
 1               5                  10                  15

Glu Ser Thr Thr Leu Thr Glu Lys Glu Gly Glu Ile Tyr Cys Lys Gly
                20                  25                  30
```

(2) INFORMATION FOR SEQ ID NO:38:

(i) SEQUENCE CHARACTERISTICS:
        (A) LENGTH: 471 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:38:

```
GTAAAAACTC GGTTCTGCTG TCTGTTAGTG TCACCAGAAA GGGAGACATC GTGCACTGTT      60

ACCTTTTGAA AATGAGACCG ACATCTTAGG ACAGTGATTA CTTCTTCCAT TCCTACTGTG     120
```

```
TGTGTTAAGT CCACACGGCT GGGGATCTGG CCGAATGGTA AAAGCTTGCC TATGTAGCAC     180

ATTCACAAGG AGGCCACGCT CAGCACGGCC TCCCCAACCT CTGACTTCCT GCTTTAAGCC     240

AAGCATATGA CTACGTGAGG GTGACACACA GAAGGCAGCT GGATTTCAGC CTGCAGCTCA     300

TCACAATCCT AACTTGGATG CCGTGGGAAT TCCTGGACTC GCTTCAAACA AGGATGCTCA     360

TAGCAGAGCC CATTTTATAT CTTAAACTGA CCTCTGCAGA GCCTCCAGTT GGCTTTTAAA     420

TTAATGGCCA TTTGTTAGTG ACCTCTGATT AACTCTCCCT TTCCTTTGTA G             471

(2) INFORMATION FOR SEQ ID NO:39:

(i) SEQUENCE CHARACTERISTICS:
        (A) LENGTH: 283 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:39:

GGTGCTACGC AAAGAACTTT GGGCCCAAGG GATTTGGCTA TGGTCAAGGG GCAGGGGCCC      60

TTGTTCATGC TCAGTAATGG TGTGAACCAG TAAGCACGAC AGAGAATCTC CATTACCAAA     120

CTGCAGATGG CGTTTATGGC GCTCACTACT GTGAAACAGC CAGCACTTGG CACTGGGCAT     180

CACCGAGCTG CCTGTGGGGG CTGGACCGAC AGCGCTGCAC TCTCCCGCCC ACTCACTAGC     240

GTCTAAGAGC ATTCTTTTAC ATTTGAAATA AAATTTTGGC TTG                      283

(2) INFORMATION FOR SEQ ID NO:40:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO:40:

Cys Tyr Ala Lys Asn Phe Gly Pro Lys Gly Phe Gly Tyr Gly Gln Gly
 1               5                  10                  15

Ala Gly Ala Leu Val His Ala Gln
                20
```